(12) United States Patent
Nittoli et al.

(10) Patent No.: US 11,596,635 B2
(45) Date of Patent: Mar. 7, 2023

(54) PHARMACEUTICAL COMPOSITIONS COMPRISING MACROLIDE DIASTEREOMERS, METHODS OF THEIR SYNTHESIS AND THERAPEUTIC USES

(71) Applicant: REGENERON PHARMACEUTICALS, INC., Tarrytown, NY (US)

(72) Inventors: Thomas Nittoli, Pearl River, NY (US); Nareshkumar F. Jain, Ringoes, NJ (US); Thomas Patrick Markotan, Newtown, PA (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 1037 days.

(21) Appl. No.: 16/189,925

(22) Filed: Nov. 13, 2018

(65) Prior Publication Data

US 2019/0151323 A1    May 23, 2019

Related U.S. Application Data

(63) Continuation of application No. 14/913,965, filed as application No. PCT/US2014/052757 on Aug. 26, 2014, now abandoned.

(60) Provisional application No. 61/934,313, filed on Jan. 31, 2014, provisional application No. 61/869,954, filed on Aug. 26, 2013.

(51) Int. Cl.
| | |
|---|---|
| *A61K 31/537* | (2006.01) |
| *A61K 31/5365* | (2006.01) |
| *A61K 47/68* | (2017.01) |
| *A61K 45/06* | (2006.01) |
| *C07D 498/18* | (2006.01) |

(52) U.S. Cl.
CPC ........ *A61K 31/537* (2013.01); *A61K 31/5365* (2013.01); *A61K 45/06* (2013.01); *A61K 47/6803* (2017.08); *A61K 47/6809* (2017.08); *A61K 47/6851* (2017.08); *C07D 498/18* (2013.01); *C07B 2200/07* (2013.01)

(58) Field of Classification Search
CPC .. A61K 31/537; A61K 31/5365; A61K 45/06; A61K 47/6803; A61K 47/6809; A61K 47/6851; C07D 498/18; C07B 2200/07; A61P 37/00; A61P 29/00; A61P 35/00; A61P 37/06

See application file for complete search history.

(56) References Cited

U.S. PATENT DOCUMENTS

| | | |
|---|---|---|
| 4,260,608 A | 4/1981 | Miyashita et al. |
| 4,361,650 A | 11/1982 | Asai et al. |
| 5,208,020 A | 5/1993 | Chari et al. |
| 5,714,586 A | 2/1998 | Kunstmann et al. |
| 6,596,541 B2 | 7/2003 | Murphy et al. |
| 7,595,292 B2 | 9/2009 | Brocchini et al. |
| 7,750,116 B1 | 7/2010 | Doronina et al. |
| 7,939,630 B2 | 5/2011 | Brocchini et al. |
| 8,816,051 B2 | 8/2014 | Brocchini et al. |
| 8,877,706 B2 | 11/2014 | Li et al. |
| 8,889,855 B2 | 11/2014 | Deng |
| 9,005,598 B2 | 4/2015 | Godwin et al. |
| 9,950,076 B2 | 4/2018 | Nittoli et al. |
| 2004/0235840 A1 | 11/2004 | Chari et al. |
| 2005/0169933 A1 | 8/2005 | Steeves et al. |
| 2007/0258987 A1 | 11/2007 | Francisco et al. |
| 2008/0171040 A1 | 7/2008 | Ebens et al. |
| 2008/0305044 A1 | 12/2008 | McDonagh et al. |
| 2008/0305497 A1 | 12/2008 | Kosmeder et al. |
| 2009/0068178 A1 | 3/2009 | Crowley et al. |
| 2009/0280056 A1 | 11/2009 | Dennis et al. |
| 2010/0129314 A1 | 5/2010 | Singh et al. |
| 2012/0058892 A1 | 3/2012 | Braun et al. |
| 2012/0096572 A1 | 4/2012 | Macdonald et al. |
| 2012/0276124 A1 | 11/2012 | Bouchard et al. |
| 2013/0029900 A1 | 1/2013 | Widdison |
| 2013/0039900 A1 | 2/2013 | Sunahara et al. |
| 2013/0101546 A1 | 4/2013 | Yurkovetskiy et al. |
| 2014/0178415 A1 | 6/2014 | Li et al. |
| 2014/0179917 A1 | 6/2014 | Deng |
| 2014/0363454 A1 | 12/2014 | Jackson et al. |

(Continued)

FOREIGN PATENT DOCUMENTS

| | | |
|---|---|---|
| CN | 103 254 311 A | 8/2013 |
| EP | 0 425 235 A2 | 5/1991 |

(Continued)

OTHER PUBLICATIONS

Grumbach, et al., LCGC, North America 2004, An Advanstar Publication, ID No. 7200001048EN (Year: 2004).*

(Continued)

*Primary Examiner* — Julie Wu
*Assistant Examiner* — John L Van Druff
(74) *Attorney, Agent, or Firm* — Squire Patton Boggs (US) LLP

(57) ABSTRACT

The disclosure relates to compositions comprising diastereomer of a macrolide exhibiting improved therapeutic profile in the context of inhibiting cell proliferation compared to the corresponding compositions comprising mixture of diastereomers. The disclosure further provides drug-ligand conjugates formed using diastereomer of the macrolide. The disclosure also provides novel method of preparation of diastereomer of the macrolide and their therapeutic uses.

12 Claims, 13 Drawing Sheets

(56) References Cited

U.S. PATENT DOCUMENTS

| | | |
|---|---|---|
| 2014/0369960 A1 | 12/2014 | Brocchini et al. |
| 2015/0056222 A1 | 2/2015 | Papadopoulos et al. |
| 2015/0125473 A1 | 5/2015 | Burt et al. |
| 2015/0157736 A1 | 6/2015 | Rabuka et al. |
| 2015/0216994 A1 | 8/2015 | Godwin et al. |
| 2015/0283259 A1 | 10/2015 | Buet et al. |
| 2016/0058882 A1 | 3/2016 | Chari et al. |
| 2016/0354482 A1 | 12/2016 | Nittoli et al. |
| 2016/0375147 A1 | 12/2016 | Nittoli |
| 2017/0121413 A1 | 5/2017 | Nittoli et al. |
| 2017/0209591 A1 | 7/2017 | Nittoli et al. |
| 2018/0289834 A1 | 10/2018 | Nittoli et al. |
| 2018/0312597 A1 | 11/2018 | Nittoli et al. |
| 2020/0121806 A1 | 4/2020 | Nittoli et al. |

FOREIGN PATENT DOCUMENTS

| | | | |
|---|---|---|---|
| WO | WO 02/094325 A2 | 11/2002 | |
| WO | WO 2005/010151 A2 | 2/2005 | |
| WO | WO 2005/089808 | 9/2005 | |
| WO | WO 2006/062779 A2 | 6/2006 | |
| WO | WO 2008/122039 | 10/2008 | |
| WO | WO 2008/141044 A2 | 11/2008 | |
| WO | WO 2009/117277 A2 | 9/2009 | |
| WO | WO-2009117277 A2 * | 9/2009 | ........... A61K 31/337 |
| WO | WO 2010/010324 | 1/2010 | |
| WO | WO 2010/126551 A1 | 11/2010 | |
| WO | WO 2011/018611 | 2/2011 | |
| WO | WO 2011/039724 A1 | 4/2011 | |
| WO | WO 2011/130598 | 10/2011 | |
| WO | WO 2012/005982 | 1/2012 | |
| WO | WO 2012/058592 A2 | 5/2012 | |
| WO | WO 2012/061590 A1 | 5/2012 | |
| WO | WO 2012/156918 A1 | 11/2012 | |
| WO | WO 2012/166559 | 12/2012 | |
| WO | WO 2012/177837 A2 | 12/2012 | |
| WO | WO 2013/053872 | 4/2013 | |
| WO | WO 2013/053873 | 4/2013 | |
| WO | WO 2013/055990 | 4/2013 | |
| WO | WO 2013/055993 | 4/2013 | |
| WO | WO 2013/068874 | 5/2013 | |
| WO | WO 2013/085925 A1 | 6/2013 | |
| WO | WO 2013/190272 A1 | 12/2013 | |
| WO | WO 2013/190292 A2 | 12/2013 | |
| WO | WO 2014/064424 A1 | 5/2014 | |
| WO | WO 2014/065661 | 5/2014 | |
| WO | WO 2014/080251 | 5/2014 | |
| WO | WO 2014/089335 A2 | 6/2014 | |
| WO | WO 2014/145090 | 9/2014 | |
| WO | WO 2014/194030 A2 | 12/2014 | |
| WO | WO 2014/197849 A2 | 12/2014 | |
| WO | WO 2014/197854 | 12/2014 | |
| WO | WO 2014/197866 A1 | 12/2014 | |
| WO | WO 2015/081282 A1 | 6/2015 | |
| WO | WO/2015/081857 | 6/2015 | |

OTHER PUBLICATIONS

Auclair, et al., PNAS 2010 vol. 107 No. 50, p. 21394-21399 (Year: 2010).*
Yoshitake, et al., Eur. J. Biochem. 1979 vol. 101, 395-399 (Year: 1979).*
Agarwal et al., "A Pictet-Spengler ligation for Protein Chemical Modification", Proc. NatL Acad. Sci., Jan. 2, 2013, vol. 110, No. 1, pp. 46-51.
Akcakanat et al. "Heterogeneous expression of GAGE, NY-ES0-.1, MAGE-A and SSX proteins in esophageal cancer: Implications for immunotherapy", Int. J. Cancer, 2006, vol. 118, pp. 123-128.
Badescu et al., "Bridging Disulfides for Stable and Defined Antibody Drug Conjugates", Bioconjugate Chemistry, May 3, 2014, vol. 25, No. 6, pp. 1124-1136, XP055165403.
Badescu, George: Director Scientific Affairs—Bioconjugation & Protein Engineering, "Producing Better ADCs Using ThioBridge™ Conjugation", ABZENA—Enabling better biopharmaceuticals, World ADC Summit of Oct. 27, 2014, San Diego, 29 pages.
Carrico et al., Introducing Genetically Encoded Aldehydes into Proteins, *Nature Chemical Biology*, Jun. 2007, vol. 3, No. 6, pp. 321-322.
Davis et al., "In Vitro Characterization of the Drug-Drug Interaction Potential of Catabolites of Antibody-Maytansinoid Conjugates", *Drug Metabolism and Disposition*, Jun. 2012, vol. 40, No. 10, pp. 1927-1934.
Del Rosario et al., "Sulfhydryl Site-Specific Cross-Linking and Labeling of Monoclonal Antibodies by a Fluorescent Equilibrium Transfer Alkylation Cross-Link Reagent", *Bioconjugate Chemistry*, 1990, vol. 1, No. 1, pp. 51-59.
Dennler et al., "Transglutaminase-Based Chemo-Enzymatic Conjugation Approach Yields Homogeneous Antibody-Drug Conjugates", *Bioconjugate Chemistry*, 2014, vol. 25, pp. 569-578.
Doronina et al, "Development of potent monoclonal antibody aurostatin conjugates for cancer therapy." *Nat. Biotech.*, 2003, vol. 21, No. 7, pp. 778-785.
Doronina et al., "Enhanced Activity of Monomethylauristatin F through Monoclonal Antibody Delivery: Effects of Linker Technology on Efficacy and Toxicity", Bioconjugate Chem. 2006, vol. 17, pp. 114-124.
Dubowchik et al, "Cathepsin b-labile dipeptide linkers for lysosomal release of doxorubicin from internalizing immunoconjugates: model studies of enzymatic drug release and antigen specific in vitro anticancer activity." *Bioconjugate Chem.*, (2002) vol. 13, pp. 855-869.
Erickson, et al., "Antibody-maytansinoid conjugates are activated in targeted cancer cells by lysosomal degradation and linker-dependent intracellular processing", Cancer Research, Apr. 15, 2006, vol. 66, No. 8, pp. 4426-4433.
Fishkin et al: "A novel pathway for maytansinoid release from thioether linked antibody-drug conjugates (ADCs) under oxidative conditions"; Chemical Communications; Jan. 1, 2011; vol. 47, No. 38, p. 10752; XP055152687.
Hans et al: "Antibody-Maytansinoid Conjugates Are Activated in Targeted Cancer Cells by Lysosomal Degradation and Linker-Dependent Intracellular Processing"; Cancer Research, American Association for Cancer Research, US; Apr. 15, 2006; vol. 66, No. 8, pp. 4426-4433, XP008074767.
Hofer et al., "An Engineered Selenocysteine Defines a Unique Class of Antibody Derivatives", *Proc. Natl. Acad. Sci.*, Aug. 26, 2008, vol. 105, No. 34, pp. 12451-12456.
Hollander et al., Selection of Reaction Additives Used in the Preparation of Monomeric Antibody-Calicheamicin Conjugates, *Bioconjugate Chemistry*, 2008, vol. 19, pp. 358-361.
International Search Report and Written Opinion in PCT/US2014/052757, dated Nov. 28, 2014, 13 pages.
International Search Report and Written Opinion in PCT/US2015/033618 dated Dec. 21, 2015, 20 pages.
International Search Report and Written Opinion of PCT/US2014/029757 dated Aug. 28, 2014, 13 pages.
International Search Report and Written Opinion of PCT/US2017/014782 dated Mar. 20, 2017, 13 pages.
Invitation together with the Search Report and Written Opinion issued by the Singapore Patent office dated Aug. 10, 2016 for the Singapore patent application No. 11201507481W; 11 pages.
Kawai et al., "Chemical Modification of Ansamitocins 3. Synthesis and Biological Effects of 3 Acyl Esters of Maytansinol", Chemical and Pharmaceutical Bulletin, *Pharmaceutical Society of Japan*, vol. 32, No. 9, Jan. 1, 1984, pp. 3441-3451, XP008094318.
Phillips et al., "Targeting HER2-Positive Breast Cancer with Trastuzumab-DM1, an Antibody-Cytotoxic Drug Conjugate", *Cancer Research*, 2008, No. 62, pp. 9280-9290. http://cancerres.aacrjournals.org/content/68/22/9280.full-text.pdf.
Pillow et al.; "Site-Specific Trastuzumab Maytansinoid Antibody-Drug Conjugates with Improved Therapeutic Activity through Linker and Antibody Engineering", Journal of Medicinal Chemistry, Oct. 9, 2014, vol. 57, No. 19, pp. 7890-7899, XP055268691.
Rabuka et al., "Site-Specific Chemical Protein Conjugation Using Genetically Encoded Aldehyde Tags", *Nat Protocols*, Dec. 1, 2012, vol. 7, No. 6, pp. 1052-1067.

(56) References Cited

OTHER PUBLICATIONS

Reddy et al., "Folate Receptor-Specific Antitumor Activity of EC131, a Folate-Maytansinoid Conjugate", Cancer Research, Jul. 1, 2007; vol. 67, No. 13; pp. 6376-6382.

Ryan et al., "Polyclonal Antibody Production Against Chito-Oligosaccharides", *Food and Agricultural Immunology,* 2001, vol. 13, pp. 127-130.

S. C. Jeffrey et al. Dipeptide-Based Highly Potent Doxorubicin Antibody Conjugates, *Bioorganic & Medicinal Chemistry Letters,* 2006, vol. 16, pp. 358-362.

Salomon et al.; "Sensitive ELISA Method for the Measurement of Catabolites of Antibody-Drug Conjugates (ADCs) in Target Cancer Cells", Molecular Pharmaceutics, Jun. 1, 2015, vol. 12, No. 6, pp. 1752-1761, XP055352192.

Sapra et al., "Monoclonal antibody-based therapies in cancer: Advances and Challenges", *Pharmacology & Therapeutics,* 2013, vol. 138, pp. 452-469.

Satyanarayanajois et al., "Medicinal chemistry for 2020", *Fut. Med. Chem.,* (Oct. 2011), vol. 3, No. 14, pp. 1765-1786.

Shaunak et al., "Site-specific PEGylation of Native Disulfide Bonds in Therapeutic Proteins", *Nature Chemical Biology,* Jun. 2006, vol. 2, No. 6, pp. 312-313.

Sun et al: "Design of Antibody-Maytansinoid Conjugates Allows for Efficient Detoxification via Liver Metabolism", Bioconjugate Chemistry; Apr. 20, 2011; vol. 22, No. 4, pp. 728-735, XP055096244.

Widdison et al., "Development of Anilino-Maytansinoid ADCs that Efficiently Release Cytotoxic Metabolites in Cancer Cells and Induce High Levels of Bystander Killing", Bioconjugate Chemistry 2015, together with Supporting Information Section, 2015, pp. 1-17, Epub ahead of print Sep. 30, 2015.

Widdison et al., "Semisynthetic Maytansine Analogues for the Targeted Treatment of Cancer"; Journal of Medicinal Chemistry, American Chemical Society, US; Jul. 13, 2006; vol. 49, No. 14; pp. 4392-4408, XP002679529.

Wolf Philipp, "Anti-psma antibody-drug conjugates and immunotoxins", Chapter 15 of Antibody-drug conjugates and immunotoxins (2012) Gail Phillips (ed), ISBN 978-1-4614-5456-4.

Zhao et al., "Synthesis and Evaluation of Hydrophilic Linkers for Antibody-Maytansinoid Conjugates", Journal of Medicinal Chemistry; May 26, 2011; vol. 54; No. 10; pp. 3606-3623; XP55046274.

Gondi et al., "Cathepsin B as a cancer target", Expert Opinion on Therapeutic Targets, 2013, vol. 17, No. 3, pp. 281-291, DOI: 10.1517/14728222.2013.740461.

Tang et al., "The Analysis of Key Factors Related to ADCs Structural Design", Apr. 2019, vol. 10, article 373, pp. 1-11, DOI: 10.3389/fphar.2019.00373.

Trail, "Antibody Drug Conjugates as Cancer Therapeutics", Antibodies 2013, 2, pp. 113-129; doi:10.3390/antib2010113.

Brocchini et al., "PEGylation of native disulfide bonds in proteins", Nature Protocols, 2006, vol. 1, No. 5, pp. 2241-2252.

Translation of Supplementary Report 2 on Invention Patent Application No. 201502765 dated Sep. 15, 2022; 9 pages.

\* cited by examiner

PHARMACEUTICAL COMPOSITIONS COMPRISING MACROLIDE DIASTEREOMERS, METHODS OF THEIR SYNTHESIS AND THERAPEUTIC USES

This Application is a continuation of U.S. Non-provisional application Ser. No. 14/913,965, filed on Feb. 23, 2016, which is a national stage entry of PCT/US2014/052757, filed on Aug. 26, 2014, which claims the benefit of priority to U.S. Provisional Application No. 61/934,313, filed on Jan. 31, 2014, and U.S. Provisional Application No. 61/869,954, filed on Aug. 26, 2013, which are all incorporated herein by reference in their entireties.

Proliferative diseases are characterized by uncontrolled growth and spread of abnormal cells. If the spread of these cells is not controlled, it can result in death. Proliferative diseases, for example cancer, can be treated by surgery, radiation, chemotherapy, hormone-based therapy and/or immunotherapy. A number of these treatments, particularly the chemotherapy, are based on the use of anti-proliferative drugs which limit the spread of the abnormal cells. Anti-proliferative drugs, however, typically are indiscriminate in their ability to kill cells, affecting both normal and abnormal cells based simply on whether a cell is replicating. Regardless, most anti-proliferative drugs require a relatively high concentration at the locale of the abnormal cell proliferation to be effective. It is this combination of providing sufficient anti-proliferative drug at a site of abnormal cell growth without also causing significant death to normal cells systemically or in the vicinity of these cells that this disclosure addresses.

Various approaches to targeted drug delivery have been tried, including the use of conjugates of tumor targeted probes (such as antibodies or growth factors) with toxins such as pseudomonas or diphtheria toxins. Conjugates for use in the treatment of cancer thereby target the anti-proliferative drug to a population of abnormal cells. Recently, conjugates that include the toxin maytansine have been employed for the treatment of cancer. Maytansine has shown great effectiveness as an anti-proliferative agent but the compound's toxicity has proven problematic toward normal cells. A need exists for developing maytansine based conjugates that have sufficient activity for use as cancer therapeutics. The more active or effective the maytansine based conjugate is at inhibiting or killing a population of abnormal cells the lower the concentration of the conjugate is required, the benefit being a reduced overall risk of damaging normal cells.

Many anti-proliferative compounds exhibit asymmetric structures, such as the Maytansinoid family of macrolides, and may therefore exist in the form of a racemic mixture, in the form of separate enantiomers with configuration "R" and "S", or (+) and (−), per stereogenic center, and various diastereomers. The present disclosure shows that targeted delivery of a single maytansinoid diastereomer exhibits improved inhibitory cell proliferation profile as compared to delivery of its respective mixture of diastereomers. Therefore, diastereomers in accordance with embodiments described herein can be used to prepare medicinal products with improved therapeutic profile that can be useful for the treatment of specific diseases and conditions, particularly cancer.

The present disclosure relates to compositions comprising a plurality of drug molecules for formula (I):

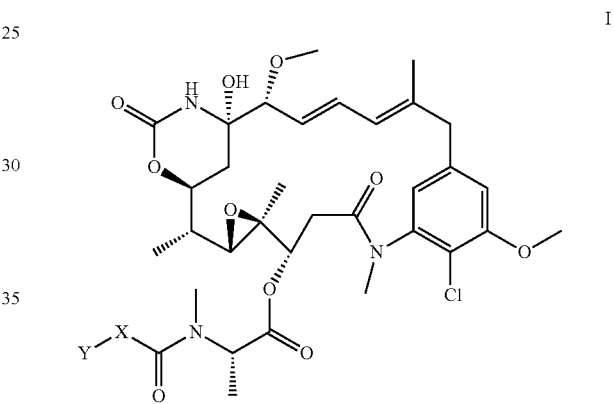

I wherein:

X is

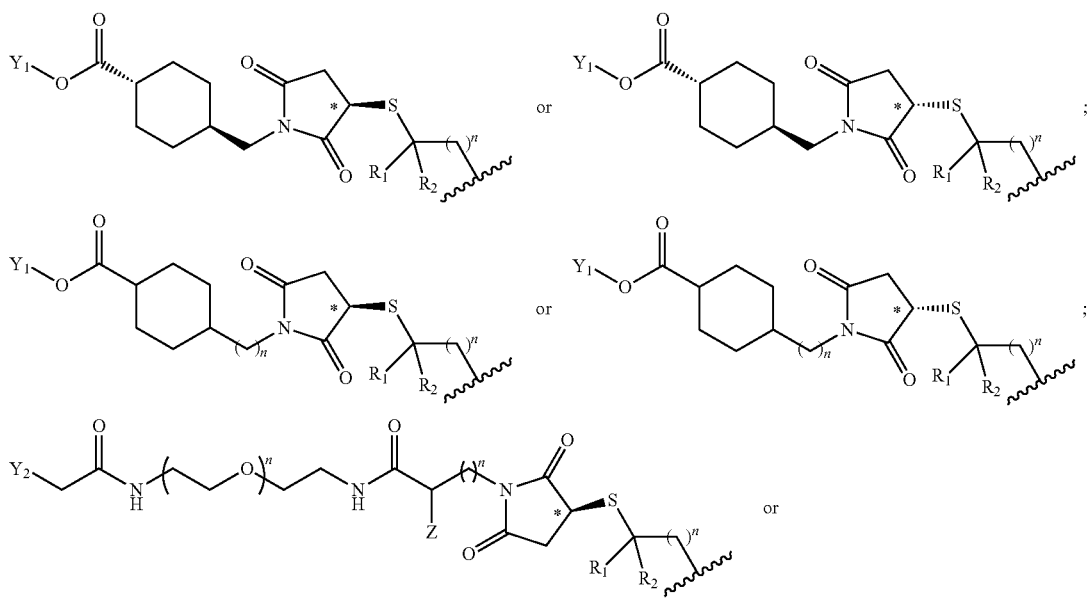

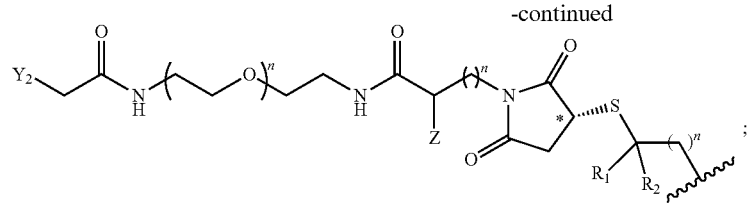;
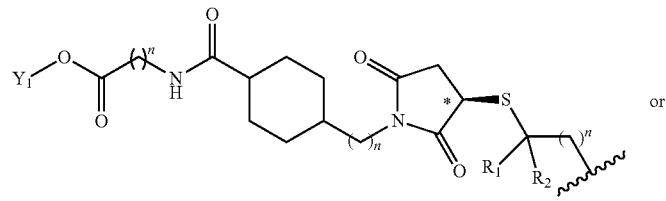 or
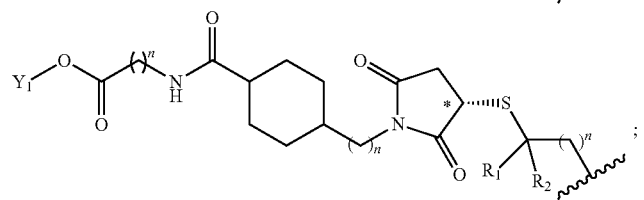;
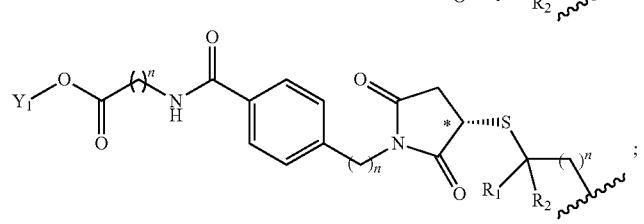 or
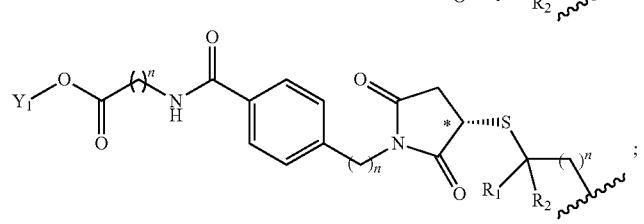;
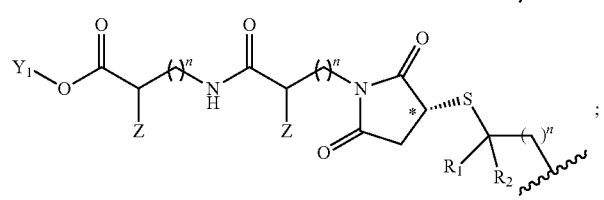 or
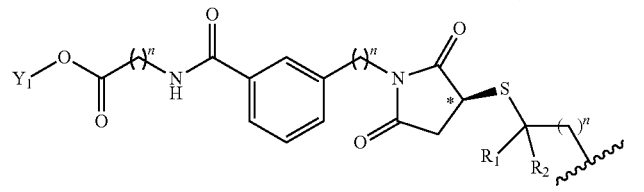;
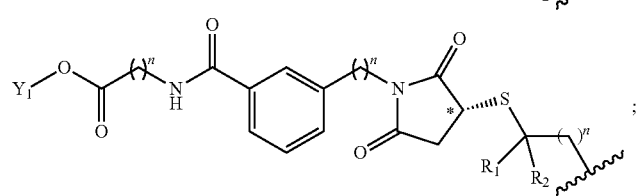 or
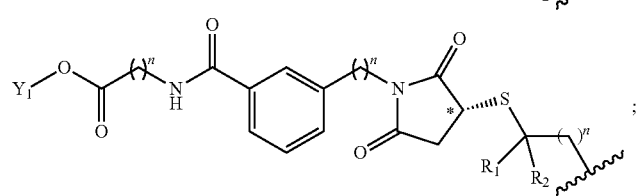;

-continued
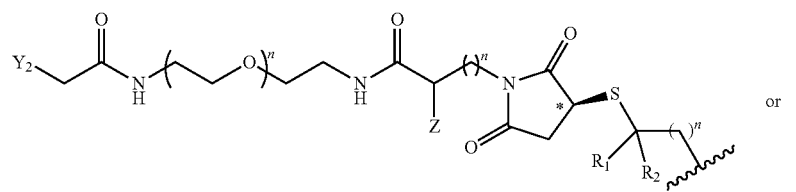 or
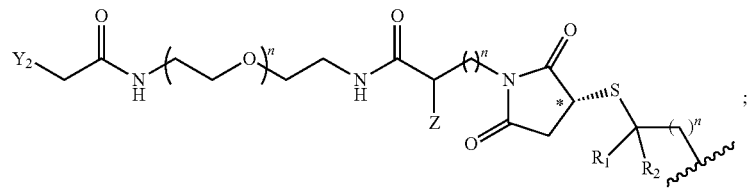 ;
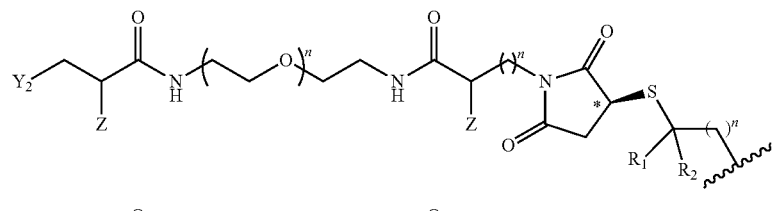 or
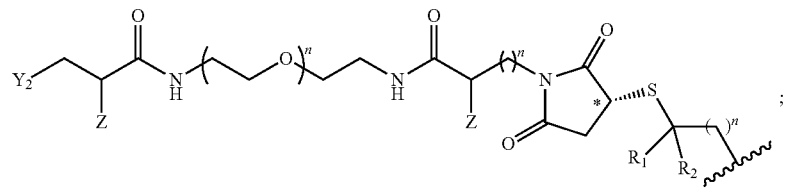 ;
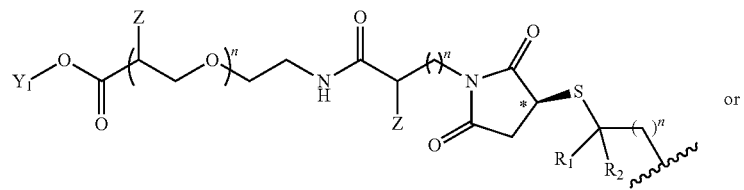 or
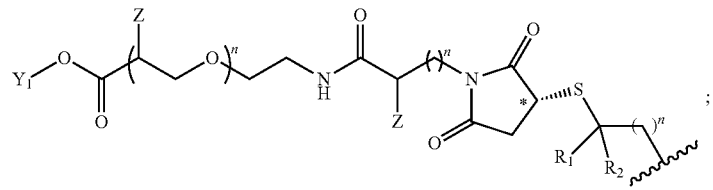 ;
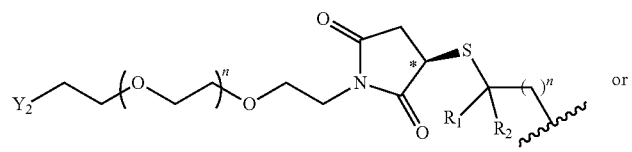 or
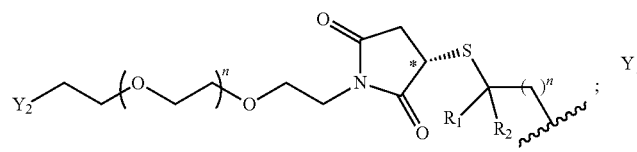 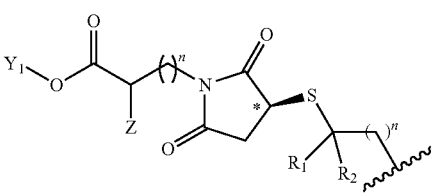 or -continued

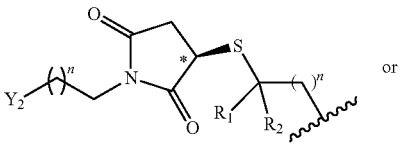

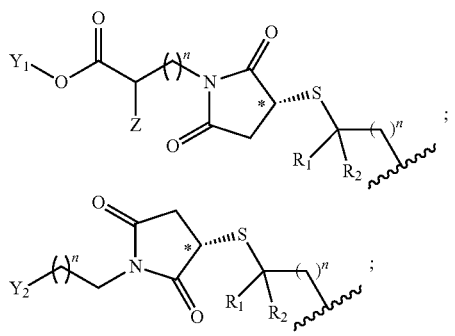

Y is $Y_1$ or $Y_2$ further wherein $Y_1$ is

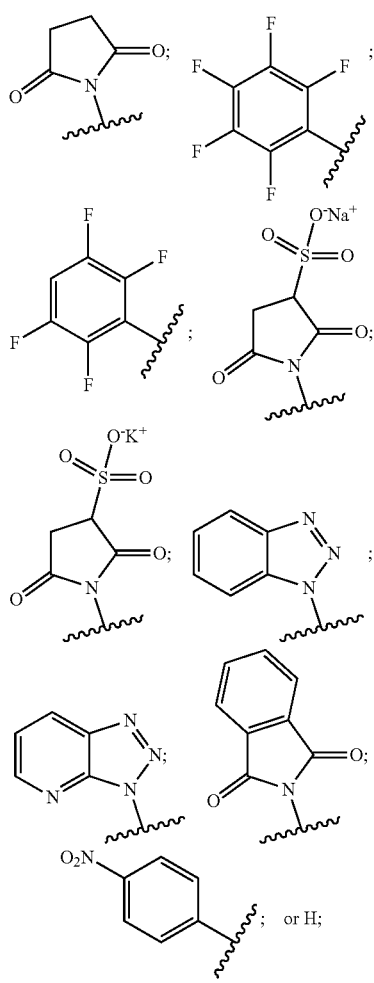

$Y_2$ is —Cl, —Br, —I, or

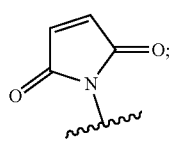 [SMILES: *N1C(=O)C=CC1=O]

Z is H or $SO_3H$;

$R_1$ and $R_2$ are independently selected from H or alkyl; each n is independently 0 or an integer from 1 to 50; and wherein the drug molecules present in the composition comprises a mixture of at least two diastereomers, a first diastereomer and a second diastereomer, further wherein said first diastereomer and second diastereomer are otherwise identical, except that said first and second diastereomers have different stereochemical configuration at a chiral carbon represented by (*) in formula X, wherein said chiral carbon atom is a carbon atom that is bound to a sulfur atom, and said first or second diastereomer is present in a diastereomeric excess of greater than 50%.

In one embodiment, the disclosure provides compositions comprising a plurality of drug molecules of formula I, wherein n is 1, and $R_1$ and $R_2$ are each independently hydrogen.

In another embodiment, the composition comprising a plurality of drug molecules of formula I are present in the composition in a diastereomeric excess of about 60%, 70%, 80%, 90%, 91%, 92%, 93%, 94%, 95%, 96%, 97%, 98%, 99% or more.

In certain embodiments, the drug molecules of formula I are present in the composition in a diastereomeric excess of from about 90% to about 100%, or from about 95% to about 100%, or from about 98% to about 100%.

In another embodiment, the composition comprising a plurality of drug molecules of formula I wherein one of the at least two diastereomers is characterized by a $^1H$ NMR spectra of FIG. 1.

As used herein, the term "about", when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

In another embodiment, the disclosure provides compositions comprising a plurality of drug molecules of formula I wherein the drug molecules are present in the composition in a diastereomeric excess of greater than 50% and show greater anti-proliferative activity than a corresponding composition comprising drug molecules of formula I that are not present in a diastereomeric excess of greater than 50%.

Further, the disclosure herein provides compositions comprising a plurality of drug molecules of formula I further comprising a therapeutically effective amount of a second or additional agent including, for example, a chemotherapeutic agent, an anti-inflammatory agent, an antibiotic, and the like.

In an embodiment, the disclosure provides compositions comprising a plurality of drug molecules of formula I represented by the following structure:
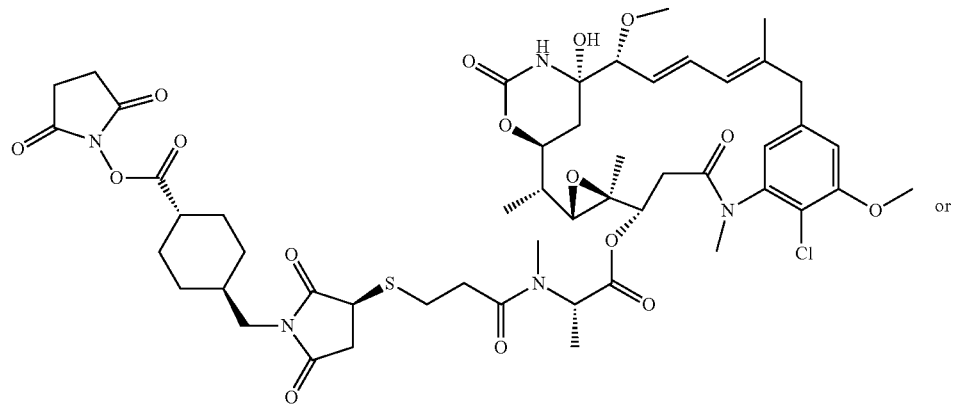
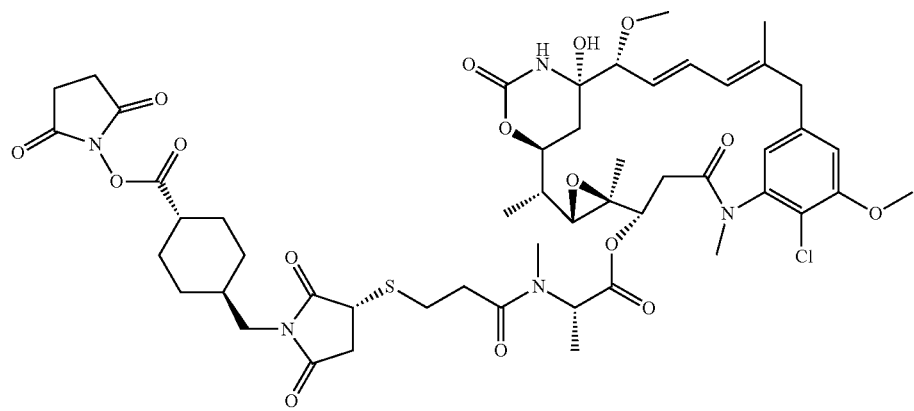
or mixtures thereof
in a diastereomeric excess of greater than 50%.
In one embodiment, one of the at least two diastereomers is a compound of formula (i)
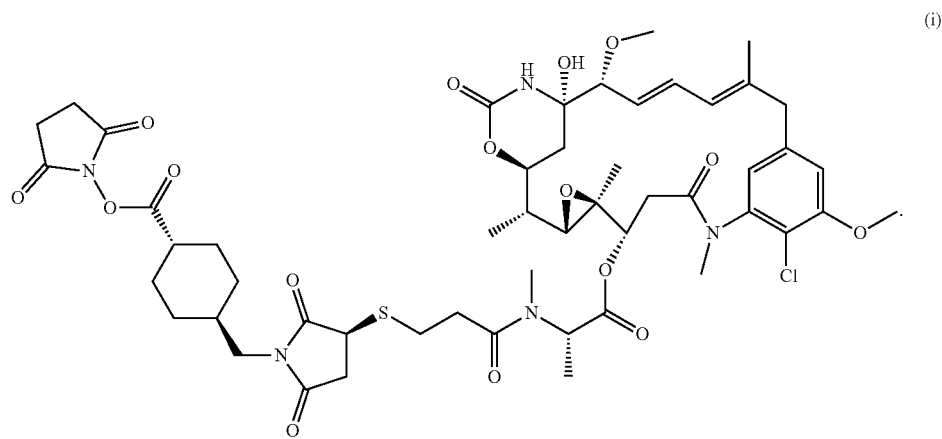 [SMILES: COc1cc2cc(c1Cl)N(C)C(=O)C[C@H](OC(=O)[C@H](C)N(C)C(=O)CCS[C@H]1CC(=O)N(C[C@H]3CC[C@H](C(=O)ON4C(=O)CCC4=O)CC3)C1=O)[C@]1(C)O[C@H]1[C@H](C)[C@@H]1C[C@@](O)(NC(=O)O1)[C@H](OC)/C=C/C=C(\C)C2]

In another embodiment, one of the at least two diastereomers is a compound of formula (ii)
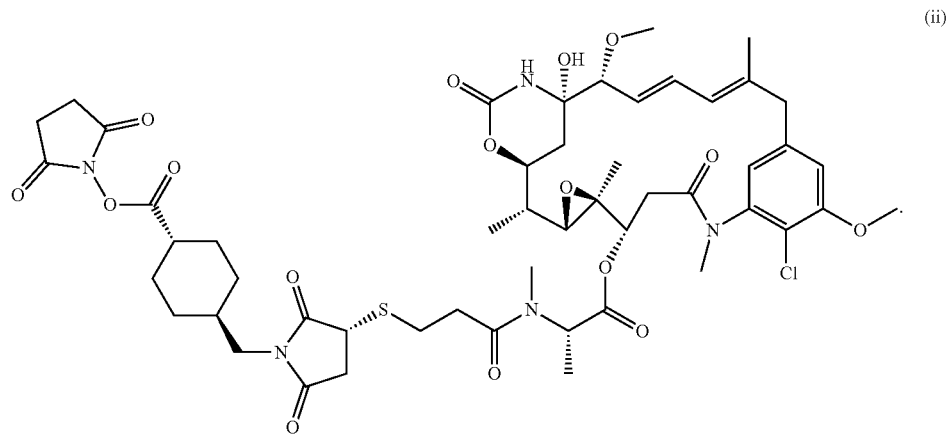
The present disclosure also provides a compound of formula (i) or (ii),
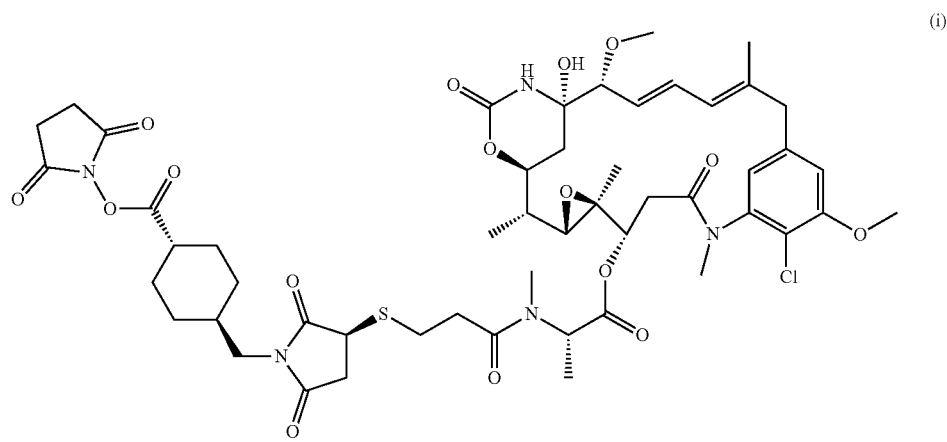
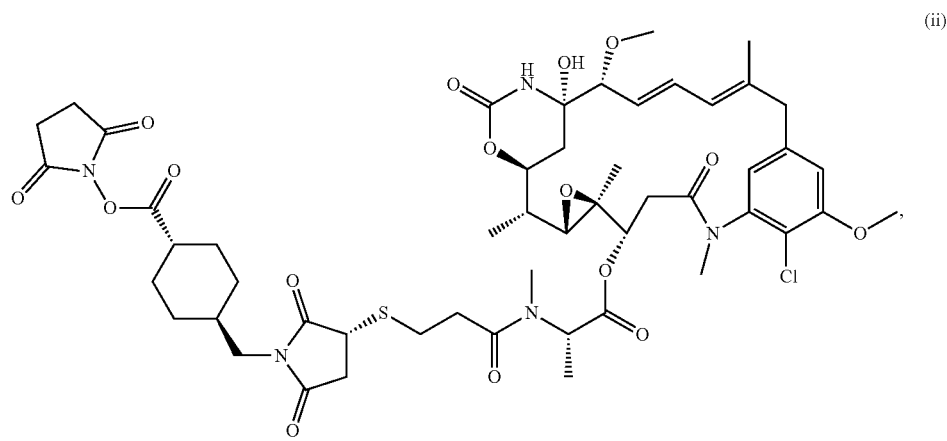 [SMILES: COc1cc2cc(c1Cl)N(C)C(=O)C[C@H](OC(=O)[C@H](C)N(C)C(=O)CCS[C@@H]1CC(=O)N(C[C@H]3CC[C@H](C(=O)ON4C(=O)CCC4=O)CC3)C1=O)[C@]1(C)O[C@H]1[C@H](C)[C@@H]1C[C@@](O)(NC(=O)O1)[C@H](OC)/C=C/C=C(\C)C2]
wherein the compound is steromerically pure.

The present disclosure also provides compositions comprising a plurality of ligand-drug conjugates of formula (II):

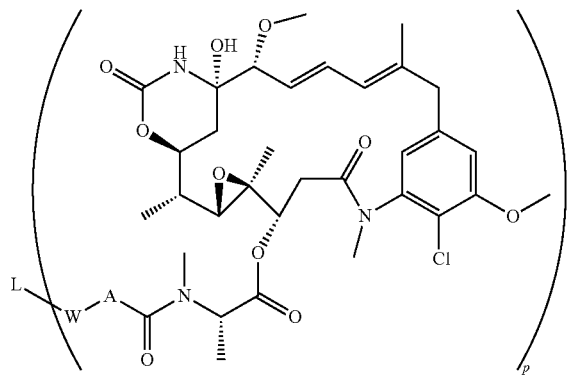

wherein:
A is

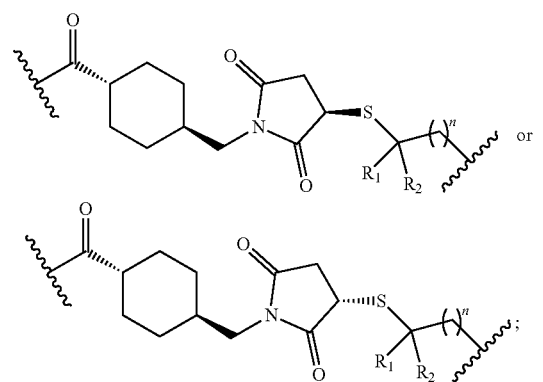

W is selected from S, O, or $NR_3$;
L is a ligand;
further wherein:
L is capable of binding to a cell or cell population;
$R_1$, $R_2$ and $R_3$ are each independently selected from H or alkyl;
n is 0 or an integer from 1 to 10;
p is an integer from 1 to 10;
and wherein the ligand-drug conjugates are present in the composition in a diastereomeric excess of greater than 50%.

In one embodiment, the disclosure provides compositions comprising a plurality of ligand-drug conjugates of formula II, wherein n is 1, and $R_1$ and $R_2$ are each independently hydrogen.

In an embodiment, the compositions comprising a plurality of ligand-drug conjugates of formula II are present in the composition in a diastereomeric excess of about 60%, 70%, 80%, 90%, 91%, 92%, 93%, 94%, 95%, 96%, 97%, 98%, 99%, or more. In certain embodiments, the drug molecules of formula II are present in the composition in a diastereomeric excess of from about 90% to about 100%, or from about 95% to about 100%, or from about 98% to about 100%.

In another embodiment, the disclosure provides compositions comprising a plurality of ligand-drug conjugates of formula II in the compositions in a diastereomeric excess of greater than 50% and show greater antiproliferative activity than a corresponding composition comprising ligand-drug conjugates of formula II that are not present in a diastereomeric excess of more than 50%.

In an embodiment, the disclosure provides compositions comprising a plurality of ligand-drug conjugates of formula II, wherein the ligand is an antibody or antigen-binding fragment thereof. The antibody or antigen-binding fragment thereof can be developed to specifically bind a tumor-associated antigen. With respect to formula II, the n can be 1, and $R_1$ and $R_2$ can each be independently a hydrogen.

In certain embodiments, the disclosure provides compositions comprising a plurality of ligand-drug conjugates of formula II, wherein the ligand is an antibody, or antigen-binding fragment thereof which specifically binds a tumor-associated antigen, and the ligand-drug conjugates are present in the composition in a diastereomeric excess of more than about 50%, 60%, 70%, 80%, 90%, 91%, 92%, 93%, 94%, 95%, 96%, 97%, 98%, 99%, or more.

In certain embodiments, the disclosure provides compositions comprising a plurality of ligand-drug conjugates of formula II, wherein the antibody, or antigen-binding fragment thereof specifically binds a tumor-associated antigen and further wherein the tumor-associated antigen is selected from the group consisting of AFP, ALK, BAGE proteins, β-catenin, brc-abl, BRCA1, BORIS, CA9, carbonic anhydrase IX, caspase-8, CD20, CD40, CDK4, CEA, CLEC12A, cMET, CTLA4, cyclin-B1, CYP1B1, EGFR, EGFRvIII, ErbB2/Her2, ErbB3, ErbB4, ETV6-AML, EphA2, Fra-1, FOLR1, GAGE proteins (e.g., GAGE-1, -2), GD2, GD3, GloboH, glypican-3, GM3, gp100, Her2, HLA/B-raf, HLA/k-ras, HLA/MAGE-A3, hTERT, IGF1R, LGR5, LMP2, MAGE proteins (e.g., MAGE-1, -2, -3, -4, -6, and -12), MART-1, mesothelin, ML-IAP, Muc1, Muc16 (CA-125), MUM1, NA17, NY-BR1, NY-BR62, NY-BR85, NY-ESO1, OX40, p15, p53, PAP, PAX3, PAX5, PCTA-1, PDGFR-α, PDGFR-β, PDGF-A, PDGF-B, PDGF-C, PDGF-D, PLAC1, PRLR, PRAME, PSMA (FOLH1), RAGE proteins, Ras, RGS5, Rho, SART-1, SART-3, Steap-1, Steap-2, survivin, TAG-72, TGF-β, TMPRSS2, Tn, TNFRSF17, TRP-1, TRP-2, tyrosinase, and uroplakin-3.

In some embodiments, the antibody, or antigen-binding fragment have amino acid sequences that vary from the above-mentioned antibodies but that retain the ability to bind a given tumor-associated antigen. Such variant antibodies and antibody fragments can comprise one or more additions, deletions, or substitutions of amino acids when compared to parent sequence, but exhibit biological activity that is essentially equivalent to that of the described antibodies.

Two conjugates are considered bioequivalent if, for example, they are pharmaceutical equivalents or pharmaceutical alternatives whose rate and extent of absorption do not show a significant difference when administered at the same molar dose under similar experimental conditions, either single dose or multiple dose. Some conjugates will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two conjugates are bioequivalent if there are no clinically meaningful differences in their safety, purity, and potency.

In one embodiment, two conjugates are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two conjugates are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the conjugate or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the conjugate (or its target) is measured as a function of time; and (d) in a well-controlled clinical trial that establishes safety, efficacy, or bioavailability or bioequivalence of a conjugate.

The present disclosure also provides a novel method for preparation of a composition comprising a plurality of drug molecules of formula (I):

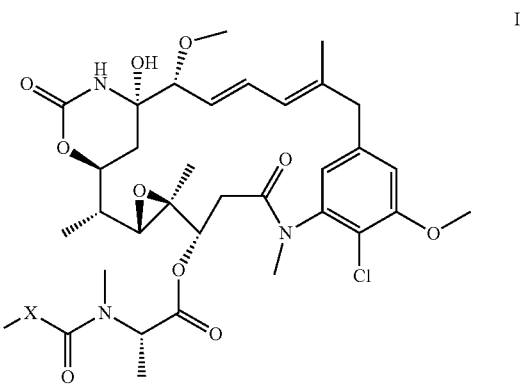

wherein:
X is

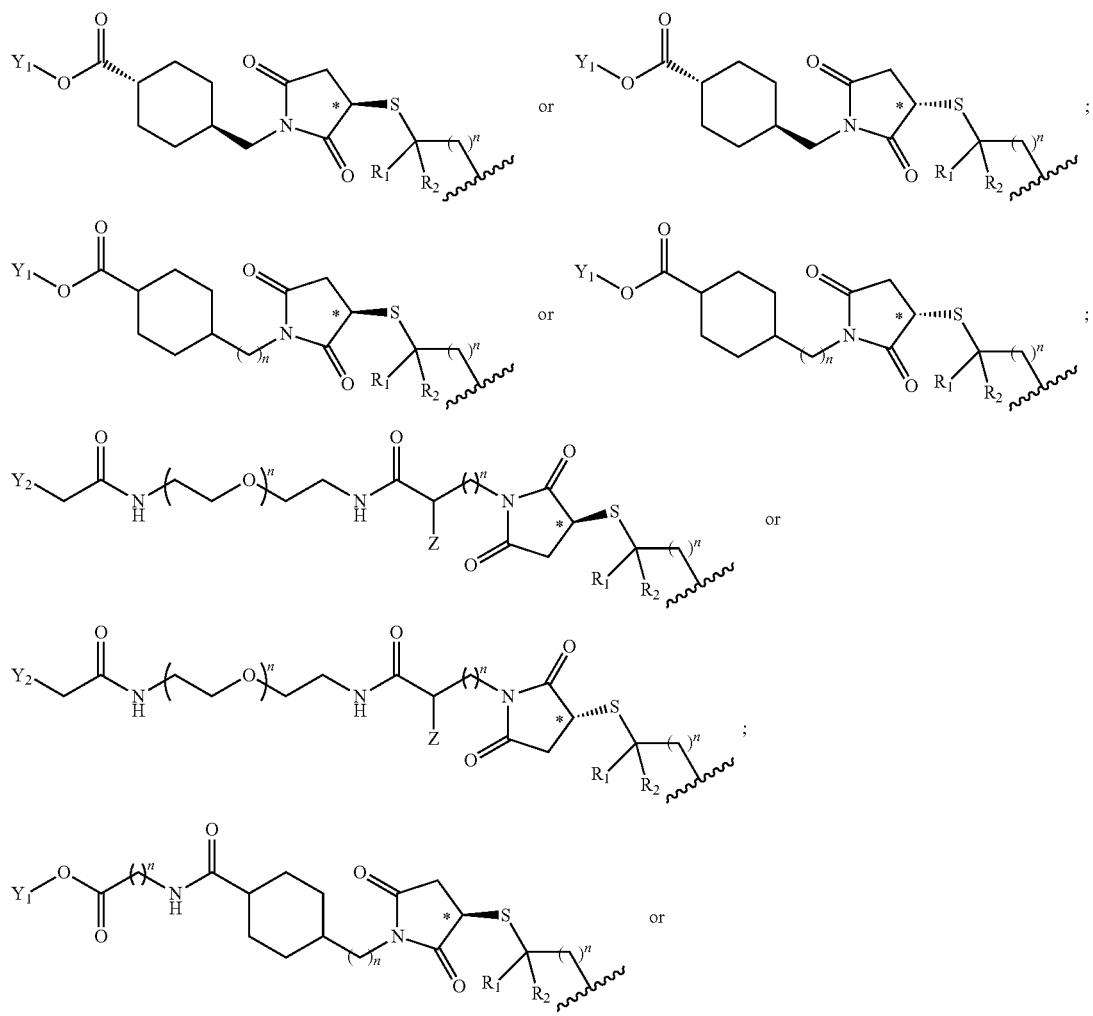

-continued
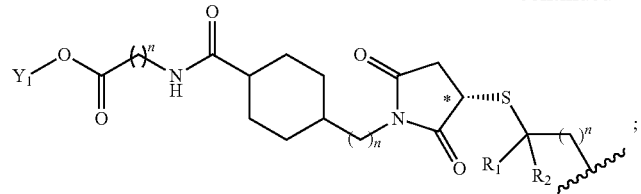
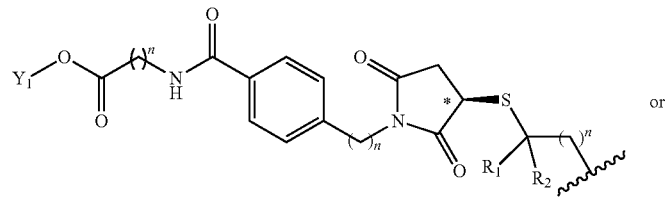
or
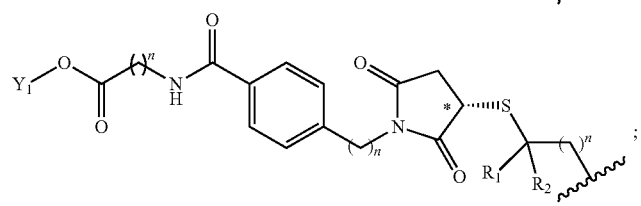
;
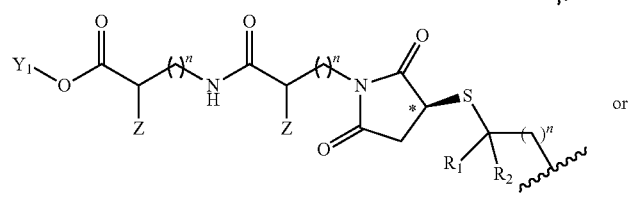
or
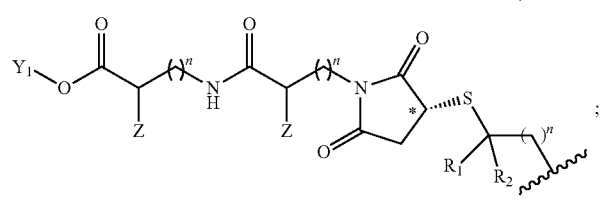
;
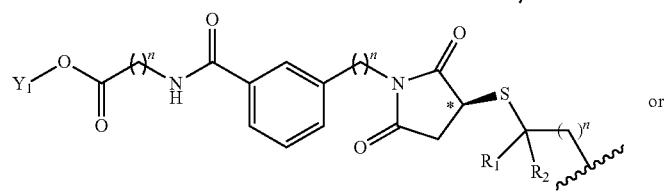
or
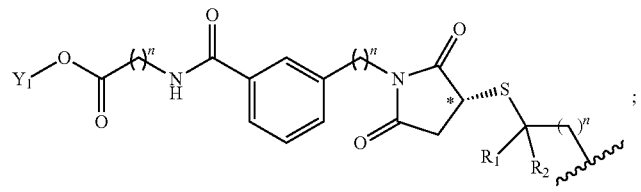
;
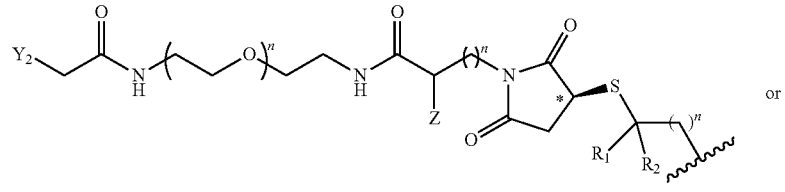
or
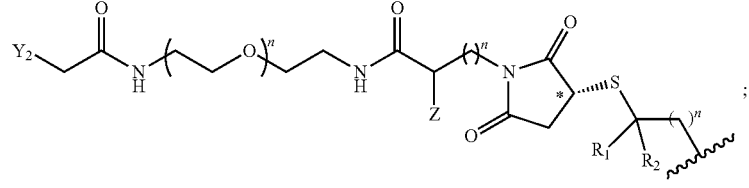
;

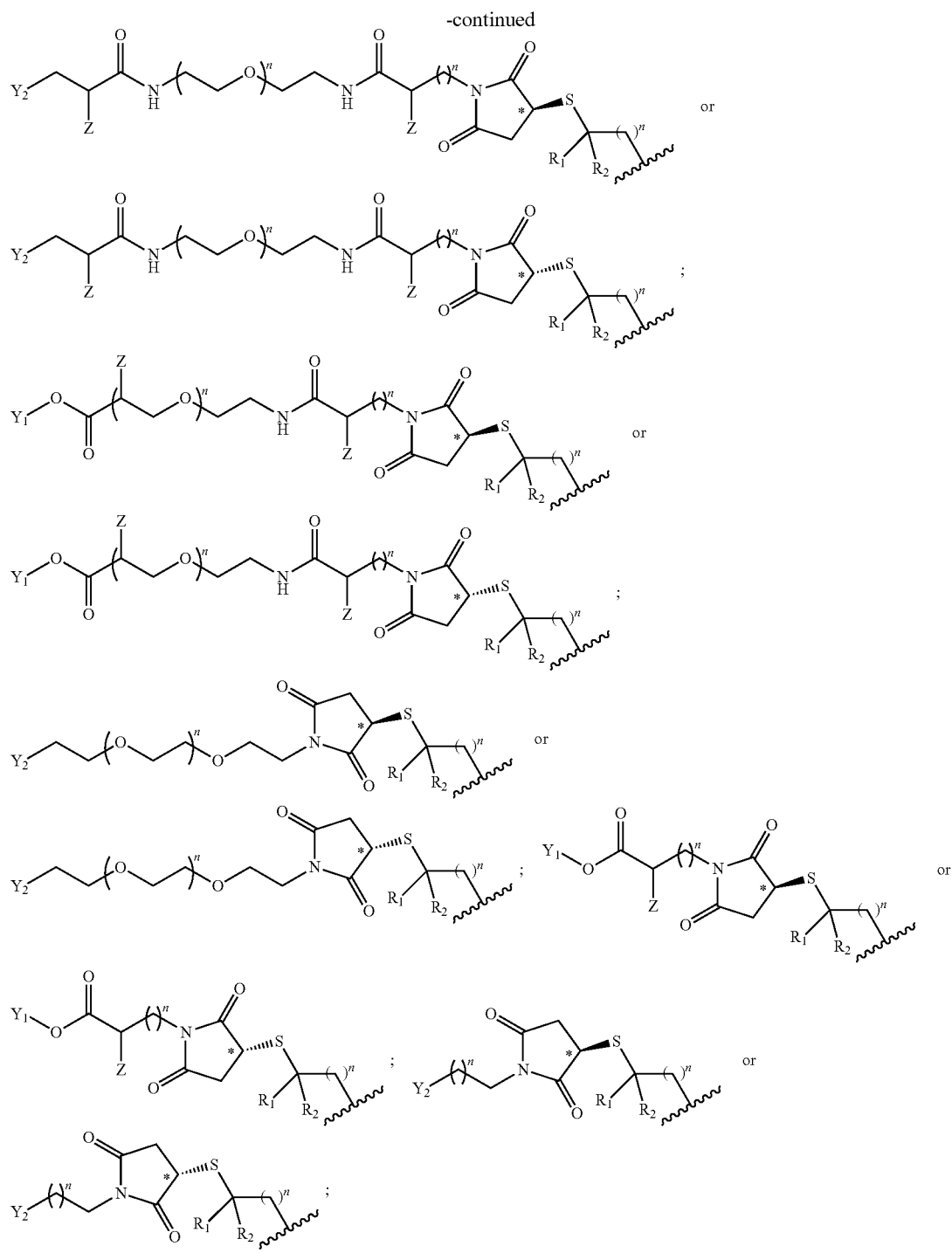
Y is $Y_1$ or $Y_2$ further wherein
$Y_1$ is

21

-continued

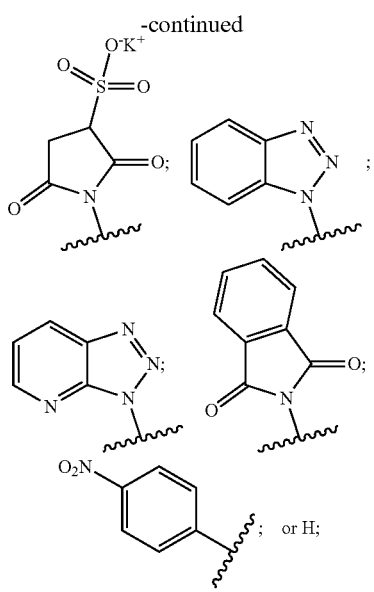

$Y_2$ is —Cl, —Br, —I, or

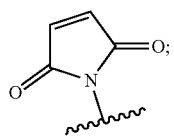 [SMILES: *N1C(=O)C=CC1=O]

$R_1$ and $R_2$ are independently selected from H or alkyl;
each n is independently 0 or an integer from 1 to 50;
and wherein the drug molecules present in the composition comprises a mixture of at least two diastereomers, a first diastereomer and a second diastereomer, further wherein said first diastereomer and second diastereomer are otherwise identical, except that said first and second diastereomers have different stereochemical configuration at a chiral carbon represented by (*) in formula X, wherein said chiral carbon atom is a carbon atom that is bound to a sulfur atom, and said first or second diastereomer is present in a diastereomeric excess of greater than 50%, the method comprising:
(a) providing a mixture comprising
  (i) a starting material which has a formula III:

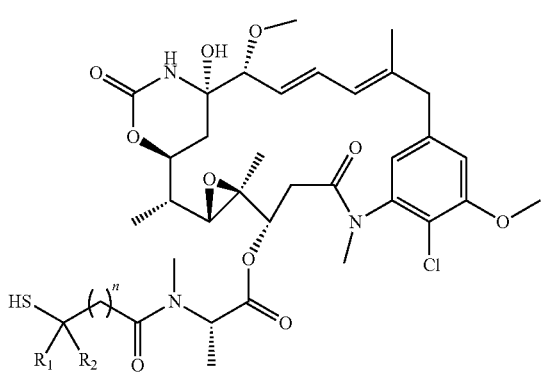

22

(ii) a compound of formula IV:

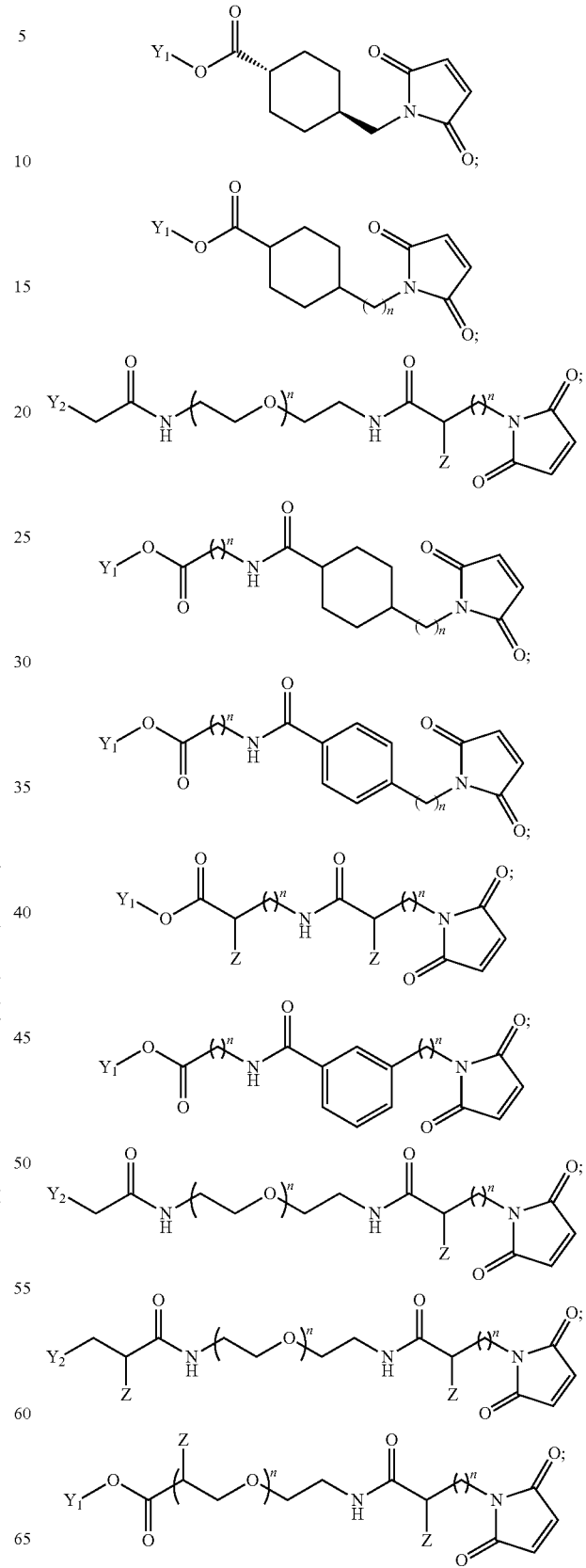

-continued

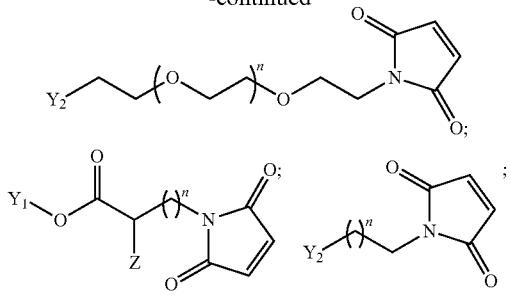

$Y_1$ is

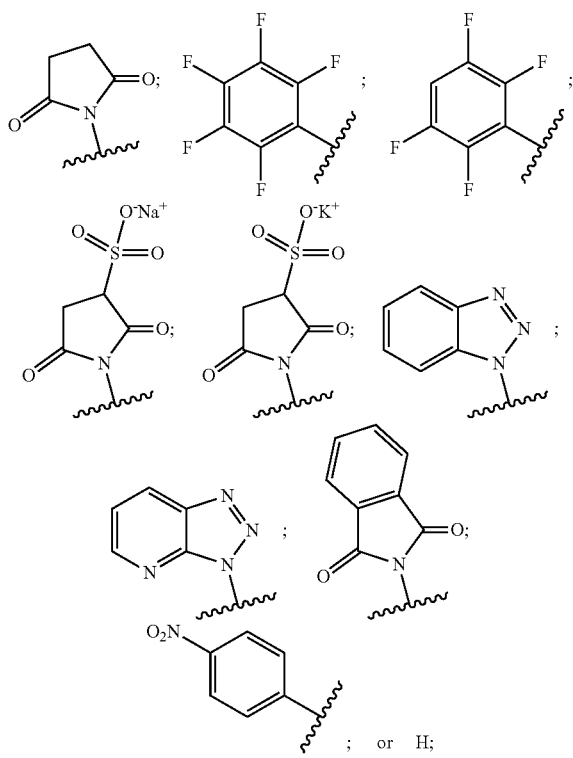
; or H;

$Y_2$ is —Cl, —Br, —I, or

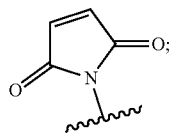 [SMILES: *N1C(=O)C=CC1=O]

Z is H or $SO_3H$;
$R_1$ and $R_2$ are independently selected from H or alkyl; and
each n is independently 0 or an integer from 1 to 50;
  (iii) an organic solvent,
  (iv) water, and
  (v) a solid substrate;
(b) allowing the mixture of step (a) to react until some of the starting material is converted to the compound of formula I; and (c) removing crude compound of formula I from the mixture of step (b).

In certain embodiments, the disclosure provides a method for preparing composition comprising a plurality of drug molecules of formula I, wherein the method further comprises step (d), further wherein step (d) comprises purifying the compound of formula I obtained in step (c) as explained above.

In certain embodiments, the disclosure provides a method for preparing compositions comprising a plurality of drug molecules of formula I, wherein the solid substrate is selected from the group consisting of silica gel, celite, alumina, a zeolite, and crushed molecular sieves. Other like solid substrates may also be utilized as long as the solid substrate allows for proper positioning of the macrolide III to allow stereoselective addition of maleimide IV.

In certain embodiments, the disclosure provides a method for preparing compositions comprising a plurality of drug molecules of formula I, wherein n is 1, and $R_1$ and $R_2$ are each independently hydrogen.

In certain embodiments, the disclosure provides a method for preparing compositions comprising a plurality of drug molecules of formula I, wherein the organic solvent comprises a polar aprotic solvent such as DMF, DMA, HMPT, NMP, acetonitrile, dioxane, acetone, DMSO, THF, ethyl acetate, methyl acetate, methylene chloride, propylene carbonate or mixtures thereof.

In certain embodiments, the disclosure provides a method for preparing compositions comprising a plurality of drug molecules of formula I, wherein the polar aprotic solvent comprises acetonitrile.

In certain embodiments, the disclosure provides a method for preparing compositions comprising a plurality of drug molecules of formula I, wherein the organic solvent and the water are present in ratio of from about 1:1 to about 4:1 or from about 1:1 to about 10:1.

In certain embodiments, the disclosure provides a method for preparing compositions comprising a plurality of drug molecules of formula I, wherein the molar ratio of the starting material having formula III and the compound of formula IV is from about 1:1 to about 1:3.

In certain embodiments, the disclosure provides a method for preparing compositions comprising a plurality of drug molecules of formula I, further comprising combining the compound of formula I with an antibody or antigen-binding fragment thereof to make an antibody-drug conjugate.

In certain embodiments, the disclosure provides a method for preparing compositions comprising a plurality of drug molecules of formula I, wherein the compound of formula I is attached to the antibody or antigen-binding fragment via an S, O, or $NR_3$.

In an embodiment, the disclosure provides a method for preparing a composition comprising a plurality of drug molecules of formula I, wherein the drug molecules of formula I are present in the composition in a diastereomeric excess of about 60% 70%, 80%, 90%, 91%, 92%, 93%, 94%, 95%, 96%, 97%, 98%, 99% or more.

In an embodiment, the disclosure provides a method for preparing compositions comprising a plurality of drug molecules of formula I represented by the following structure:

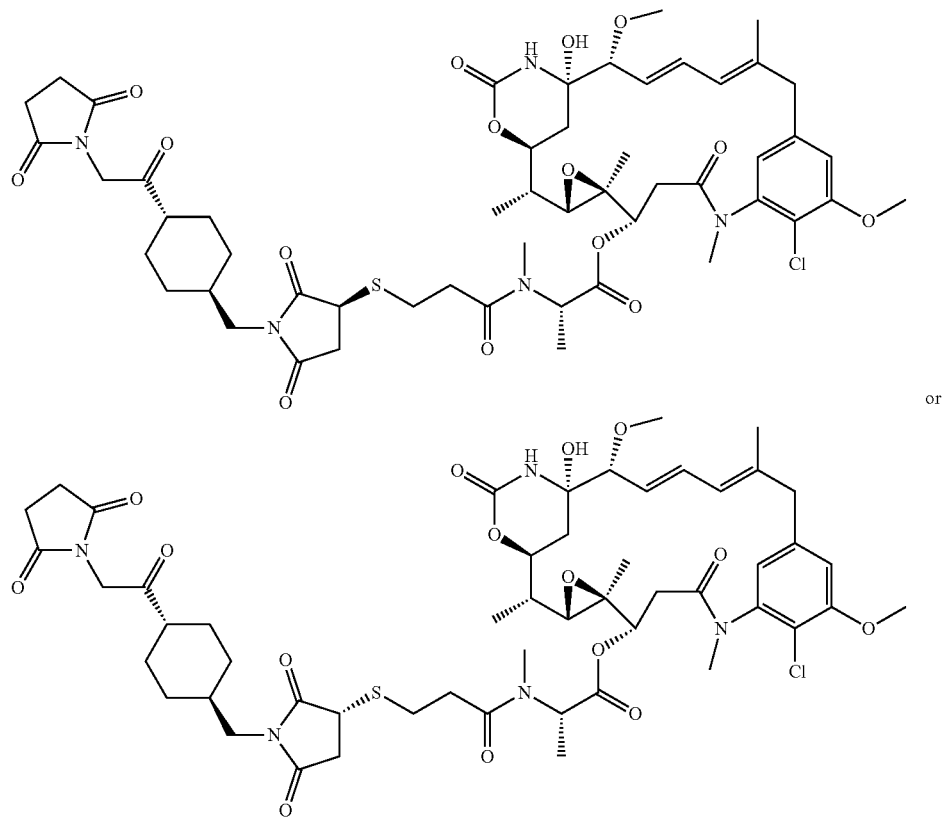

or in a diastereoselective excess of greater than 50%. Although certain exemplary methods for preparing the compositions of the present invention are set forth in the working examples herein, other methods are contemplated within the scope of the present invention such as, e.g., chromatographic separation of a racemic mixture or mixture of diastereomers (e.g., HPLC on normal, reverse, or chiral stationary phase using polar aprotic solvent mixtures, etc.).

The present disclosure also relates to compositions wherein a plurality of the drug molecules of formula I, or the ligand-drug conjugates of formula II, are contained within the compositions in a therapeutically effective amount, and further comprising a pharmaceutically acceptable diluent, carrier or excipient.

In an embodiment, the disclosure provides compositions comprising a plurality of drug molecules of formula II further comprising a therapeutically effective amount of a second chemotherapeutic agent.

In numerous embodiments, the compositions comprise a compound of formula (I) and/or (II) of the present disclosure which may be administered in combination with one or more additional compounds or therapies. Co-administration and combination therapy are not limited to simultaneous administration, separately or together, but also include sequential administrations.

Combination therapy includes administration of a single pharmaceutical dosage formulation which contains a composition comprising one or more compounds of formula (I) and/or (II) and one or more other therapeutic agents; as well as administration of a composition comprising compound of formula (I) and/or (II) of the present disclosure and one or more additional agent(s) in its own separate pharmaceutical dosage formulation. For example, a composition comprising a compound of formula (I) and/or (II) and, a cytotoxic agent, a chemotherapeutic agent, or a growth inhibitory agent can be administered to the patient together in a single dosage composition such as a combined formulation, or each agent can be administered in a separate dosage formulation. Where separate dosage formulations are used, a composition comprising a compound of formula (I) and/or (II) and one or more additional agents can be administered concurrently, or separately at staggered times, i.e., sequentially.

Non-limiting examples of such additional therapeutic agents include cytokine inhibitors (e.g., an interleukin-1 (IL-1) inhibitor (such as rilonacept or anakinra, a small molecule IL-1 antagonist, or an anti-IL-1 antibody); IL-18 inhibitor (such as a small molecule IL-18 antagonist or an anti-IL-18 antibody); IL-4 inhibitor (such as a small molecule IL-4 antagonist, an anti-IL-4 antibody or an anti-IL-4 receptor antibody); IL-6 inhibitor (such as a small molecule IL-6 antagonist, an anti-IL-6 antibody or an anti-IL-6 receptor antibody); aspirin; NSAIDs; steroids (e.g., prednisone, methotrexate, etc.); low dose cyclosporine A; tumor necrosis factor (TNF) or TNF receptor inhibitors (e.g., a small molecule TNF or TNFR antagonist or an anti-TNF or TNFR antibody); uric acid synthesis inhibitors (e.g., allopurinol); uric acid excretion promoters (e.g., probenecid, sulfinpyrazone, benzbromarone, etc.); other inflammatory inhibitors (e.g., inhibitors of caspase-1, p38, IKK1/2, CTLA-4Ig, etc.); and/or corticosteroids. The additional therapeutic agent(s) may be administered prior to, concurrent with, or after the administration of the one or more compounds of formula (I) and/or (II) (for purposes of the present disclosure, such administration regimens are considered the administration of one or more compounds of formula (I) and/or (II) "in combination with" a therapeutic agent).

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL®, Bristol-Myers Squibb Oncology, Princeton, N.J.) and docetaxel (TAXOTERE®; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

A "growth inhibitory agent" when used herein refers to a compound or composition which inhibits growth of a cell, especially a cancer cell either in vitro or in vivo. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C.

The present invention also provides pharmaceutical compositions. Such compositions comprise a therapeutically effective amount of an active agent and a pharmaceutically acceptable carrier. The term "pharmaceutically acceptable" means approved by a regulatory agency of the United States Federal or State government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In an embodiment, the composition is formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents of the disclosure can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the active agent of the disclosure, which will be effective in the treatment of a medical condition, can be determined by standard clinical techniques based on the present description. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally about 0.5 to 20 milligrams of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

In one embodiment, the disclosure provides a method of treatment of a medical disorder in an individual suffering from the medical disorder comprising administering to the individual an effective amount of a composition comprising a compound of formula (I) and/or (II), and further comprising administering sequentially or consecutively an additional therapy or administering at least one additional therapeutic agent.

In another embodiment, the disclosure relates to a method of treating a disease sensitive to treatment with said method, said method comprising parenterally administering to a patient in need thereof a therapeutically effective dose of the composition comprising a compound of formula (I) and/or (II).

The present disclosure further includes the use of any of the compositions comprising compounds of formula (I), formula (II), formula (i), formula (ii), or a combination thereof and/or pharmaceutical formulations thereof in the manufacture of a medicament for the treatment, prevention and/or amelioration of a medical disorder.

The present disclosure further includes the use of any of the compositions comprising compounds of formula (I), formula (II), formula (i), formula (ii), or a combination thereof and/or pharmaceutical formulations thereof in the manufacture of a medicament for the treatment, prevention and/or amelioration of a tumor.

While the embodiments herein have predominantly been described in relation to antiproliferative disorders such as cancer, it is envisioned that the compositions herein can also be useful in the treatment of a medical disorder selected from autoimmune diseases and other immunological diseases and dysfunctions, inflammatory diseases, infectious diseases, neurodegenerative diseases, bone disorders, and cardiovascular diseases. Further, any disorder that can benefit from the targeted delivery of a toxic substance to particular cells, cell types, tissues and/or organs is within the scope of the present invention.

Finally, embodiments herein may include compositions comprising mixtures of compounds as represented by formula (I) and formula (II).

The references to certain embodiments made in the following description are considered illustrative only of the principles of the disclosure. Further, since numerous modifications and changes will readily be apparent to those skilled in the art, it is not intended to limit the disclosure to the exact construction and process shown as described herein. Accordingly, all suitable modifications and equivalents may be resorted to as falling within the scope of the disclosure and as defined by the claims that follow.

The words "comprise", "comprising", "include" and "including" when used in this specification and in the following claims are intended to specify the presence of the stated features, integers, components, or steps, but they do not preclude the presence or addition of one or more additional features, integers, components, or steps thereof.

General terms used in any of the embodiments herein can be defined as follows; however, the meaning stated should not be interpreted as limiting the scope of the term per se.

The term "conjugate" as used herein refers to compound having a Ligand, linker and Biologically Active Molecule. Illustrative examples include compounds of formula (II).

The term "spacer" as used herein refers to chemical building blocks of the linker used to spatially separate the Ligand from the Biologically Active Molecule and to allow for catabolism of the linker inside of cells.

The term "macrolide" as used herein refers to any Biologically Active Molecule having a macrolide ring.

The symbol ⟶ denotes the points of attachment.

The term "alkyl" as used herein refers to a hydrocarbon radical having a straight or branched chain or combinations thereof. Alkyl radicals can be a univalent, a bivalent or a cyclic radical. Examples of univalent alkyl radicals are methyl, ethyl, 1-propyl, 2-propyl, n-butyl, isobutyl, sec-butyl, t-butyl, pentyl, neopentyl, hexyl, isohexyl, and the like. As a way of illustration examples of bivalent alkyl radicals include

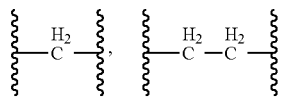

Examples of cyclic alkyl radicals include cyclopropyl, cyclobutyl, cyclopentyl, cyclohexyl, and the like. Typical alkyl radicals have from one to ten carbon atoms, one to nine carbon atoms, one to eight carbon atoms, one to seven carbon atoms, one to six carbon atoms, one to five carbon atoms, one to four carbon atoms, one to three carbon atoms, one to two carbon atoms or one carbon atom. Typical cycloalkyl are 3 to 7 member monocyclic ring radicals.

The phrase "pharmaceutically acceptable salt" as used herein refers to both organic and inorganic salts of the conjugate compounds described herein, e.g., compounds of formula (I), and (II). The salts are pharmaceutically acceptable and include: sulfate, citrate, nitrate, phosphate, ascorbate, bromide, gluconate, benzoate, oxalate, pantothenate, and the like. Note that pharmaceutically acceptable salts herein may include more than one charged atom in its structure as well as one or more counter ion. Preparation of conjugate compounds herein as pharmaceutically acceptable salts is well known to one of skill in the art.

The term "ligand" as used herein means any molecule or compound that specifically or selectively interacts with and/or binds to a second molecule or compound. In certain embodiments, a ligand is an antibody or antigen-binding fragment thereof. Other examples of ligands suitable for use in the context of the present invention include, e.g., aptamers, peptides that specifically interact with a particular antigen (e.g., peptibodies), receptor molecules, and antigen-binding scaffolds (e.g., DARPins, HEAT repeat proteins, ARM repeat proteins, tetratricopeptide repeat proteins, and other scaffolds based on naturally occurring repeat proteins, etc., [see, e.g., Boersma and Pluckthun, 2011, *Curr. Opin. Biotechnol.* 22:849-857, and references cited therein]).

Antibodies exist as intact immunoglobulins, or as a number of well-characterized fragments produced by digestion with various peptidases. For example, pepsin digests an antibody below the disulfide linkages in the hinge region to produce F(ab)'$_2$, a dimer of Fab which itself is a light chain joined to V$_H$—C$_H$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv (scFv) single variable domains (Dabs)) or those identified using display libraries such as phage, E. coli or yeast display libraries (see, for example, McCafferty et al. (1990) Nature 348:552-554).

Methods for preparing antibodies are known to the art. See, for example, Kohler & Milstein (1975) Nature 256: 495-497; Harlow & Lane (1988) *Antibodies: a Laboratory Manual*, Cold Spring Harbor Lab., Cold Spring Harbor, N.Y.). Antibodies that are isolated from organisms other than humans, such as mice, rats, rabbits, cows, can be made more human-like through chimerization or humanization.

The term "human antibody" as used herein is intended to include antibodies having variable and constant regions derived from human immunoglobulin sequences. The human mAbs of the invention may include amino acid residues not encoded by human immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species have been grafted onto human FR sequences.

The term "therapeutically effective amount" as used herein refers to an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

The term "racemate" as used herein means an equimolar mixture of a pair of enantiomers. The term racemate also refers to a racemic mixture.

The term "enantiomer" as used herein refers to compounds which non-superimposable with the mirror images of each other Enantiomers may exist in either the (R) or (S) configuration.

The term "stereoselective synthesis" refers to a chemical reaction that leads to formation of a single stereoisomer or an enantiomer-enriched mixture of isomers from among two or more possible stereoisomers.

The term "diastereomeric excess" refers to the difference between the mole fraction of the desired single diastereomer as compared to the remaining diastereomers in a composition. Diastereomeric excess is calculated as follows:

(amount of single diastereomer)−(amount of other diastereomers)/1

For example, a composition that contains 90% of 1 and 10% of 2, 3, 4, or a mixture thereof has a diastereomeric excess of 80% [(90−10)/1]. A composition that contains 95% of 1 and 5% of 2, 3, 4, or a mixture thereof has a diastereomeric excess of 90% [(95−5)/1]. A composition that contains 99% of 1 and 1% of 2, 3, 4, or a mixture thereof has a diastereomeric excess of 98% [(99−1)/1]. The diastereomeric excess can similarly be calculated for any one of 1, 2, 3, or 4.

The term "stereomerically pure" as used herein refers to a compound wherein the indicated stereoisomer is present to a greater extent than other stereoisomers of that compound, e.g., the compound is present in diastereomeric excess. In some embodiments, the stereomerically pure compounds described herein comprise 80% or greater, 85% or greater, 90% or greater, 95% or greater, or 97% or greater by weight of one stereoisomer of the compound.

Conjugates in accordance with various embodiments described herein can be prepared by any known method in the art. An illustrative protocol for producing conjugates is provided in the Examples below.

In one embodiment, the conjugates can be prepared by i) reacting a Ligand with drug molecules of formula (I) to form a conjugate of formula (II), and ii) purifying the conjugate.

In an alternative embodiment, the conjugates are prepared by reacting a Ligand, linker and biologically active macrolide in a single reaction. Once the conjugates in accordance with the invention are prepared they can be purified.

In one embodiment, the compositions comprising drug molecules of formula (I) and/or compositions comprising conjugate compounds of formula (II) described herein can be evaluated for their ability to suppress proliferation of various cancer cell lines in vitro. For example, compositions comprising drug molecules or formula (I) and/or compositions comprising conjugate compounds of formula (II) can be applied to in vitro plated cancer cells for a predetermined number of days and surviving cells measured in assays by known methods.

The above specification, examples and data provide a complete description of the manufacture and use of the composition of the invention. Since many embodiments of the invention can be made without departing from the spirit and scope of the invention, the invention resides in the claims hereinafter appended.

All references cited herein and in the Examples that follow, including patents, published patent applications, and literature references, are expressly incorporated by reference in their entireties.

The description and Examples presented infra are provided to illustrate the subject invention. One of skill in the art will recognize these Examples are provided by way of illustration only and are not included for the purpose of limiting the invention.

Embodiments disclosed herein are illustrated in greater detail by means of the non-limiting examples described below.

EXAMPLES

Experimental Details

Figure 1:
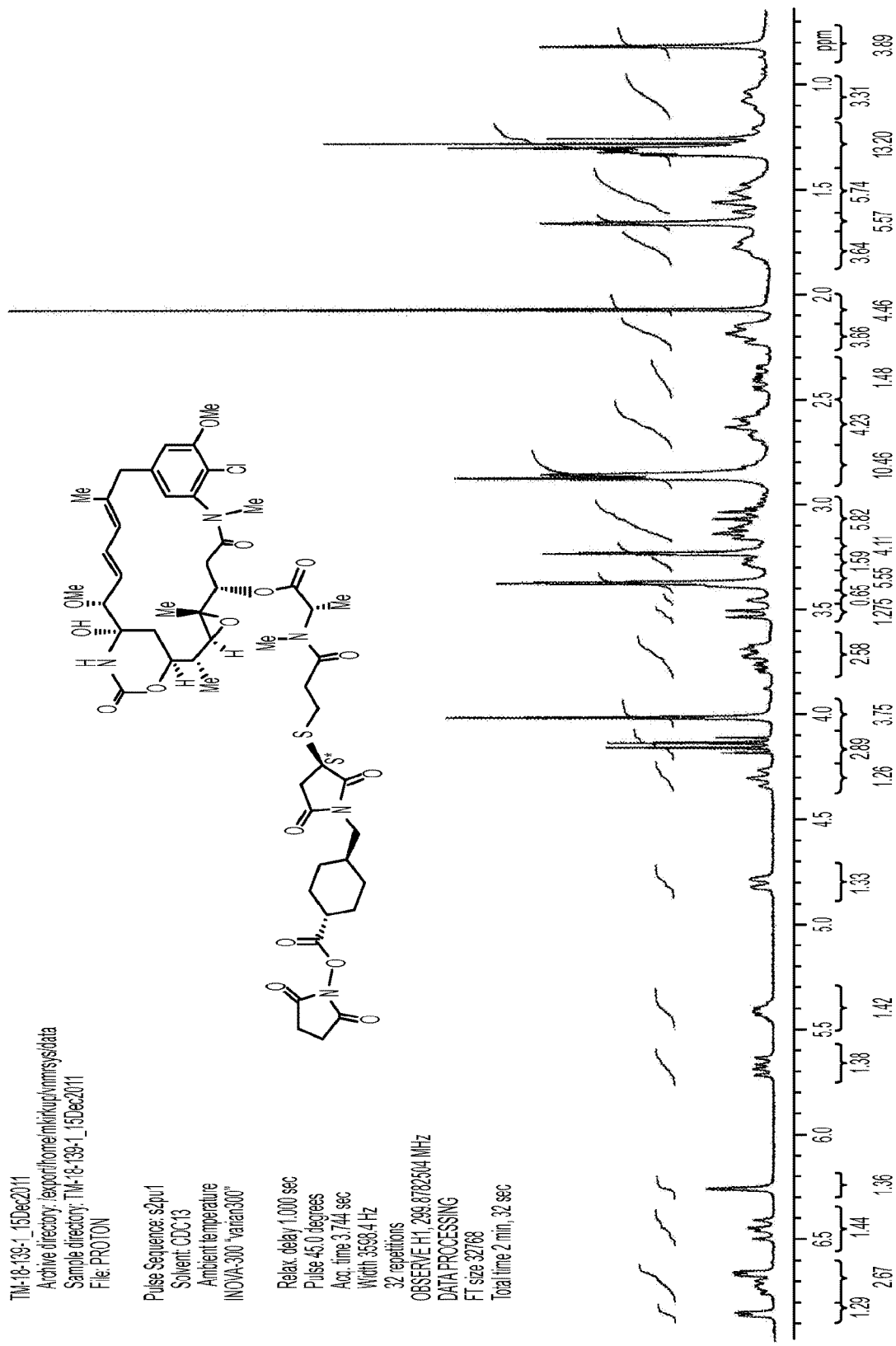
FIG. 1 illustrates an $^1$H-NMR spectrum of Maytansin-3-N-methyl-L-alanine-propanamidyl-3-thio-3-succinimidyl-N-methylcyclohexyl-4-trans-carboxysuccinate (5). The $^1$H-NMR spectrum is consistent with a single diastereomer present in at least 95% diastereomeric excess since the spectrum is not complicated by resonances attributable to the other diastereomer. (For comparative purposes Example 2 sets forth the $^1$H-NMR spectrum of the mixture of diastereomers).

Proton NMR spectra (for compounds that could not be detected by UV) were acquired on a Varian Inova 300 MHz instrument, while mass spectra were collected on an Agilent 1100 series LC/MSD with electrospray ionization source and quadrupole ion trap analyzer. All conjugates were analyzed using a Bruker ultraFleXtreme MALDI-TOF-TOF mass spectrometer. All starting materials and solvents were purchased commercially and used without purification, unless otherwise noted.

Example 1

Synthesis of Maleimidylmethyl-4-trans-cyclohexyl-carboxy-succinate (3): Maleimidylmethyl-4-trans-cyclohexanecarboxylic acid (2)

The title compound was prepared in two steps (Step A and Step B) using modified versions of the methods described by Marnett et al. (*J. Med. Chem.*, 1996, 39, 1692-1670).

Step A:

A solution of trans-4-aminomethylcyclohexane carboxylic acid (7.00 g, 44.5 mmol) in 1,4-dioxane (70 mL) was treated with maleic anhydride (4.89 g, 49.9 mmol) and stirred at ambient temperature for 48 h. The reaction was evaporated in vacuo to a white solid that can be stored or carried on to the next step without further purification. ¹H NMR (300 MHz, DMSO-d₆) δ 9.11 (m, 1H), 6.44 (d, 1H, J=13 Hz), 6.24 (d, 1H, J=13 Hz), 3.05 (t, 2H, J=6 Hz), 2.13 (tt, 1H, J=12 Hz, 4 Hz), 1.90 (m, 2H), 1.75 (m, 2H), 1.44 (m, 1H), 1.28 (m, 2H), 0.96 (m, 2H).

Step B:

The maleamic acid from Step A (36.8 g, 144 mmol) and sodium acetate (13.6 g, 165 mmol) were dissolved in acetic anhydride (368 mL), sealed in a glass reaction vessel, and heated to 120° C. for 3 hours. The cooled reaction mixture (a black syrup) was poured onto water (3 L), stirred, and extracted with dichloromethane. The organic layer was dried over Na₂SO₄, filtered over a sintered glass funnel, and the clear filtrate evaporated and dried under high vacuum giving the title compound as a yellow solid (7.00 g, 20%). ¹H NMR (300 MHz, CDCl₃) δ 6.73 (s, 2H), 3.40 (d, 2H, J=7 Hz), 2.28 (m, 1H), 2.06 (m, 2H), 1.75 (m, 3H), 1.42 (m, 2H), 1.03 (m, 2H).

Maleimidylmethyl-4-trans-cyclohexanecarboxysuccinate (3)

The product of the preceding step B (10.0 g, 42.1 mmol) was dissolved in dichloromethane (50 mL) under Ar, treated with N-hydroxysuccinimide (7.27 g, 63.2 mmol) and 1-(3-dimethylaminopropyl)-3-ethylcarbodiimide hydrochloride (EDAC, 12.4 g, 64.5 mmol), and the reaction was stirred at ambient temperature overnight. The resulting brown solution was diluted with dichloromethane, washed with water and brine, dried over Na₂SO₄, filtered over a sintered glass funnel, and the filtrate concentrated and dried in vacuo. This product was then dissolved in hot ethyl acetate, treated with activated charcoal (1.5 g), filtered, and the filtrate cooled. Filtration of the crystalline product, washing with cold ethyl acetate, and suction drying then gave the title compound as a tan solid (5.52 g, 39%). ¹H NMR (300 MHz, CDCl₃) δ 6.72 (s, 2H), 3.42 (m, 2H), 2.85 (br s, 4H), 2.56 (tt, 1H, J=12 Hz, 4 Hz), 2.18 (m, 2H), 1.80 (m, 2H), 1.70 (m, 1H), 1.56 (m, 2H), 1.09 (m, 2H).

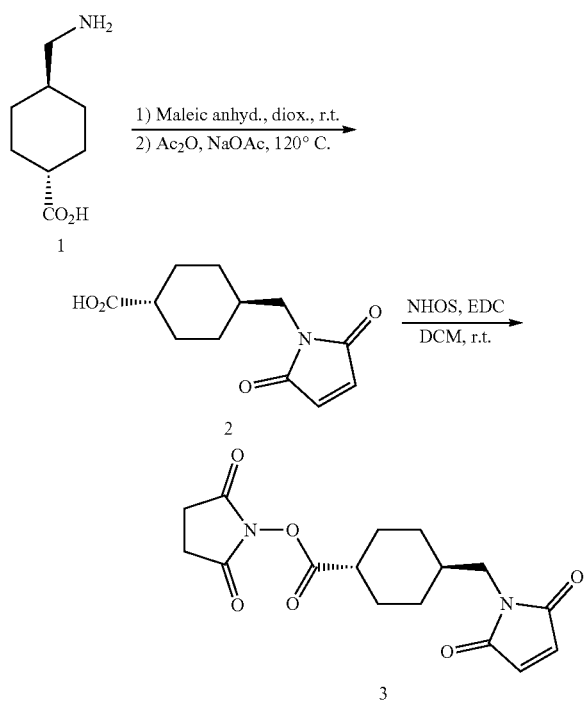

Example 2

Maytansin-3-N-methyl-L-alanine-propanamide-3-thiol (4)

The title compound, known in the art as DM1, was prepared using a modified version of the method described by Whitesides et al. (*J Org. Chem.*, 1991, 56, 2648-2650). Maytansin-3-N-methyl-L-Ala-(3-methyldisulfanyl) propanamide (DM1-SMe, 2.42 g, 3.09 mmol, prepared in a manner similar to Ho and Carrozzella, U.S. Pat. Appl. 2007/0037972 A1) was dissolved in acetonitrile (30 mL), treated with a solution of tris(2-carboxyethyl)phosphine hydrochloride (8.23 g, 28.7 mmol) in water (30 mL), the pH was raised to ca. 3 with the addition of saturated aqueous NaHCO$_3$ (5 mL), the flask was purged with Ar, and the reaction was stirred at ambient temperature under a rubber septum (vented due to effervescence). After 2 h, the reaction was treated with brine (ca. 100 mL), bubbled with Ar for 5 minutes (to remove the free methylmercaptan), and the phases separated. The aqueous phase was extracted twice with ethyl acetate (EtOAc), saturated with NaCl, and extracted twice more with EtOAc. The combined organic layers were then dried over Na$_2$SO$_4$, filtered, and the filtrate concentrated and dried in vacuo to give the title compound as a white solid (2.24 g, 98%). $^1$H NMR (300 MHz, CDCl$_3$/CD$_3$OD) δ 6.76 (d, 1H, J=1.5 Hz), 6.63 (d, 1H, J=11 Hz), 6.59 (d, 1H, J=1.5 Hz), 6.35 (m, 2H), 5.59 (dd, 1H, J=15 Hz, 9 Hz), 5.36 (q, 1H, J=6.5 Hz), 4.68 (dd, 1H, J=12 Hz, 3 Hz), 4.21 (t, 1H, J=10 Hz), 3.92 (s, 3H), 3.60 (d, 1H, J=13 Hz), 3.42 (d, 1H, J=9 Hz), 3.29 (s, 3H), 3.14 (s, 3H), 3.05 (d, 1H, J=13 Hz), 2.95 (d, 1H, J=10 Hz), 2.77 (s, 3H), 2.75-2.47 (m, 6H), 2.11 (dd, 1H, J=14 Hz, 3 Hz), 1.58 (s, 3H), 1.47 (d, 1H, J=14 Hz), 1.40 (m, 1H), 1.22 (m, 6H), 0.73 (s, 3H). MS (ESI, pos.): calc'd for C$_{35}$H$_{48}$ClN$_3$O$_{10}$S, 737.3; found 738.3 (M+H), 720.3 (M−H$_2$O+H).

Maytansin-3-N-methyl-L-alanine-propanamidyl-3-thio-3-succinimidyl-N-methylcyclohexyl-4-trans-carboxysuccinate (5)

The following procedure describes a new method not known in the art. The product of the preceding step (4, 2.23 g, 3.02 mmol) and Maleimidylmethyl-4-cyclohexanecarboxysuccinate (3, 1.50 g, 4.49 mmol) were dissolved in 4:1 acetonitrile/water (75 mL), treated with fine silica gel scraped from a preparative TLC plate (11.2 g), the flask purged with Ar, and the mixture stirred at ambient temperature under rubber septum. After 18 hours, more 3 (0.77 g, 2.3 mmol) and acetonitrile (MeCN, 10 mL) were added, and the reaction stirred an additional 6 hours. The mixture was filtered over Celite, solids washed with MeCN and ethyl acetate (EtOAc), and the filtrate concentrated in vacuo to a gold solid, which was purified by flash column chromatography on an 120 g silica gel cartridge (50-100% 1:1 EtOAc/MeCN in dichloromethane over 33 min, 75 mL/min). Evaporation and drying of the pure column fractions in vacuo gave the title compound as a cream-colored solid (2.09 g). Concentration of the impure fractions and repurification on an 80 g silica gel cartridge as above gave an additional batch of cream-colored solid (0.22 g), and brought the total yield of title compound to 2.31 g (71%). $^1$H NMR (300 MHz, CDCl$_3$) δ 6.85 (d, 1H, J=4 Hz), 6.72 (m, 1H), 6.65 (d, 1H, J=4 Hz), 6.44 (dd, 1H, J=15 Hz, 11 Hz), 6.25 (s, 1H), 5.67 (dd, 1H, J=16 Hz, 9 Hz), 5.41 (m, 1H), 4.79 (d, 1H, J=11 Hz), 4.30 (t, 1H, J=11 Hz), 3.72 (m, 2H), 3.51 (d, 1H, J=9 Hz), 3.37 (m, 4H), 3.27 (m, 1H), 3.23 (s, 3H), 3.16-2.99 (m, 4H), 2.85 (m, 7H), 2.62 (m, 3H), 2.39 (ddd, 1H, J=19 Hz, 12 Hz, 4 Hz), 2.18 (br m, 2H), 1.77 (br m, 3H), 1.66 (s, 3H), 1.60-1.47 (m, 4H), 1.31 (m, 6H), 1.05 (m, 2H), 0.82 (s, 3H). MS (ESI, pos.): calc'd for C$_{51}$H$_{66}$ClN$_5$O$_{16}$S, 1071.4; found 1072.4 (M+H), 1054.9 (M−H$_2$O+H); [α]$^{20}_{589\ nm}$=−52.4 (c=0.00301, MeOH). See FIG. 1 for $^1$H-NMR of single diastereomer.

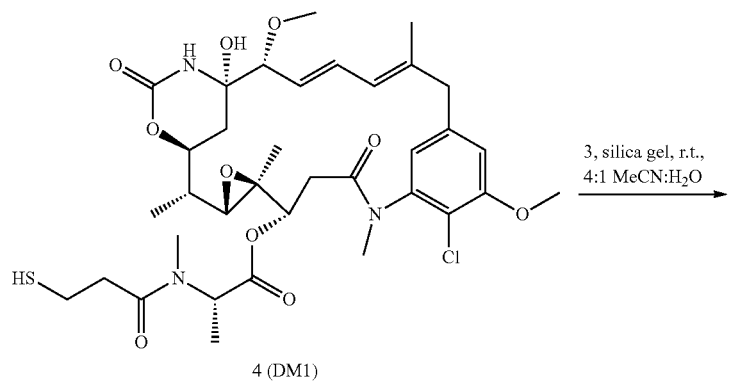

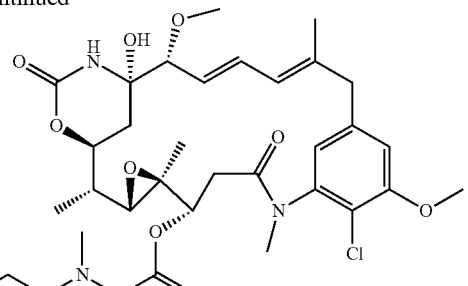

5

Example 3

Mixture of diastereomers of Maytansin-3-N-methyl-L-alanine-propanamidyl-3-thio-3-succinimidyl-N-methylcyclohexyl-4-trans-carboxysuccinate (6)

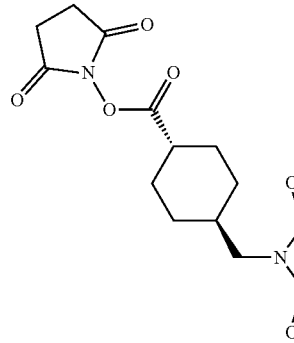

Figure 2:
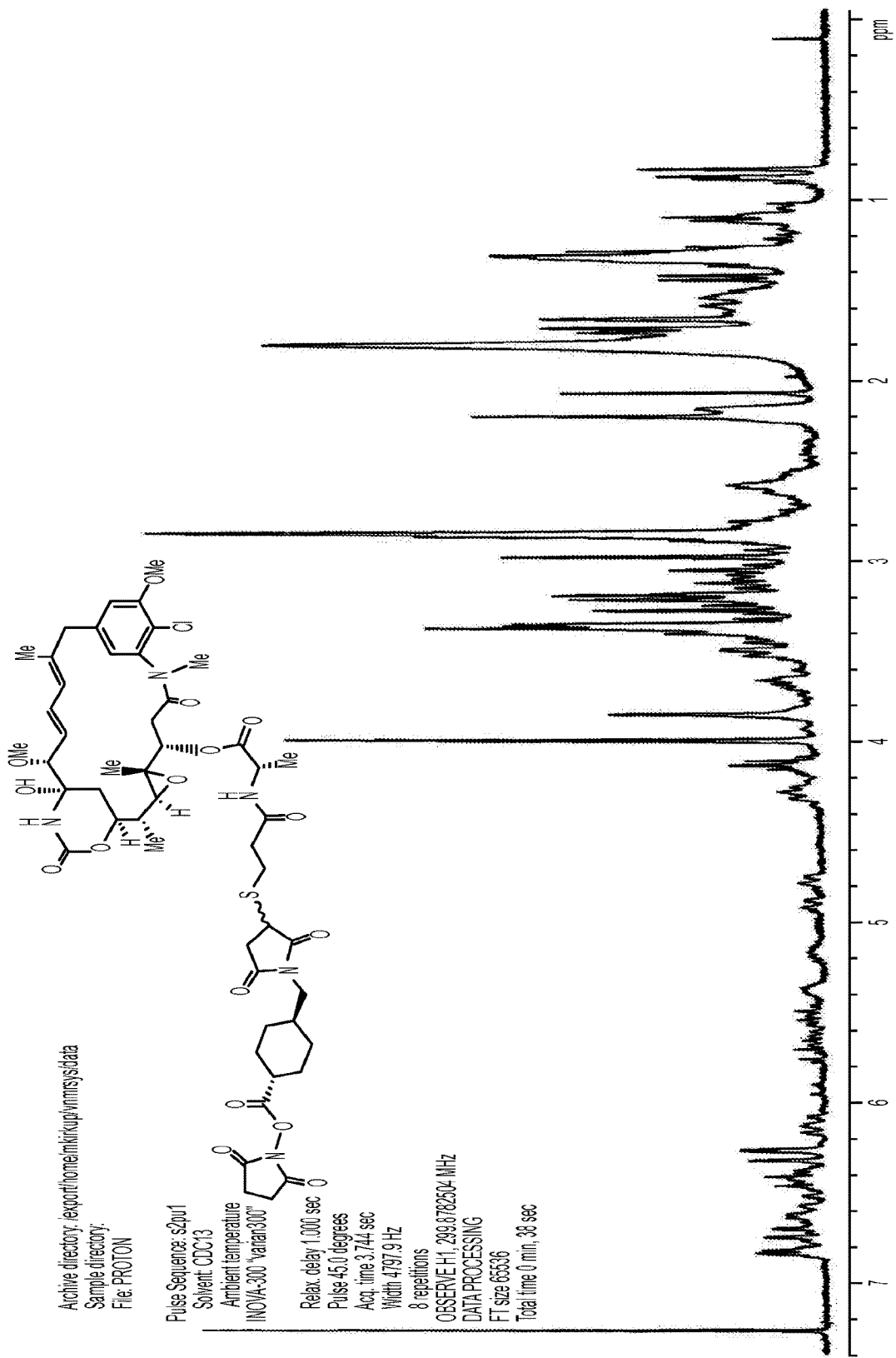
FIG. 2 illustrates an ¹H-NMR spectrum of mixture of diastereomers of Maytansin-3-N-methyl-L-alanine-propanamidyl-3-thio-3-succinimidyl-N-methylcyclohexyl-4-trans-carboxysuccinate (6).

A sample of the mixed stereoisomers of 5 was synthesized according to US Patent Application 20100129314, Example XI. $^1$H NMR (300 MHz, CDCl$_3$) δ 6.85-6.6 (m), 6.4 (m), 6.1 (m), 5.8-5.4 (m), 5.2 (m), 4.92-4.79 (m), 4.4-4.1 (m), 4.03 (s), 3.82 (m), 3.8-2.2 (m), 2.1 (m), 2.07 (s), 2.0-0.8 (m). MS (ESI, pos.): calc'd for C$_{51}$H$_{66}$ClN$_5$O$_{16}$S, 1071.4; found 1072.4 (M+H). See FIG. 2 for $^1$H-NMR of mixture of diastereomers.

Example 4

Racemic Maytansin-3-N-methyl-L-alanine-propanamidyl-3-thio-3-succinimidyl-N-methylcyclohexyl-4-trans-carboxylic acid (8)

A solution of trans-1,4-(maleimidomethyl) cyclohexane-1-carboxylic acid 7 (167 mg, 0.701 mmol) in 1, 2-dimethoxyethane (8 mL) was added to a solution of 4 (340 mg, 0.461 mmol) in 1, 2-dimethoxyethane (15 mL). The mixture was then treated with pH 7.5 buffer (20 mL) and a few drops of saturated aqueous NaHCO$_3$ to maintain the pH. The reaction mixture was stirred overnight at room temperature under argon and then concentrated under reduced pressure. The crude residue was purified by reverse phase chromatography using a C18 column, 20-40 micron column (100 g), eluting with a gradient (10 95% over 25 mins) of acetonitrile (0.1% AcOH) in water (0.1% AcOH), and lyophilized to give 8 (330 mg, 0.338 mmol, 73% yield) as a white solid. MS m/z: 977.2 [MH+], 957.2 [M−18], 999.2 [M+Na]; Purity: >98% (by LC/MS).

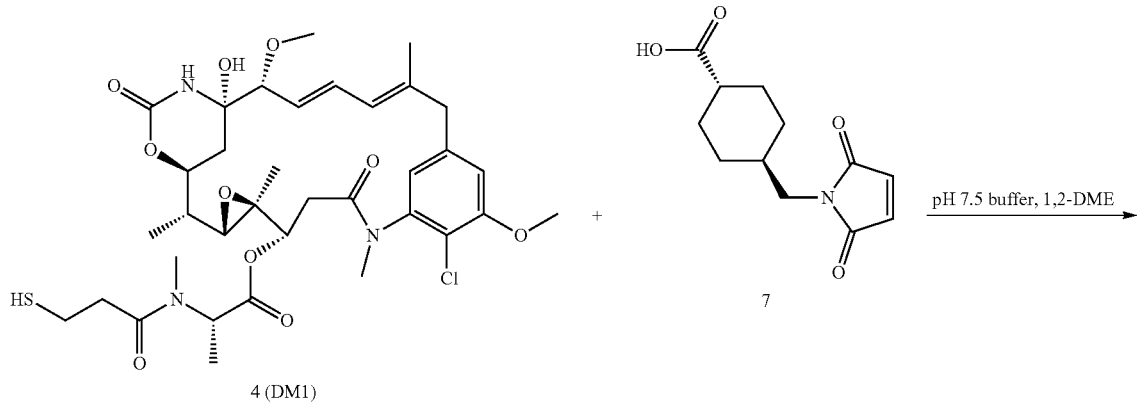

-continued

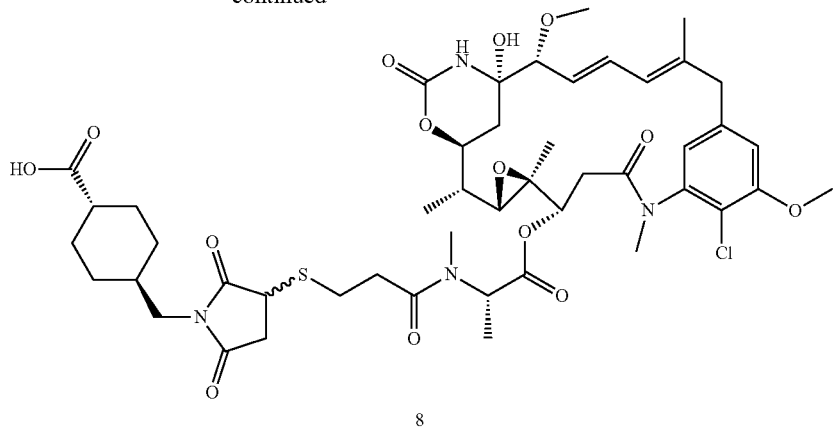

8

Example 5

Chiral Separation of 8 to Single Diastereomers (R*)-Maytansin-3-N-methyl-L-alanine-propanamidyl-3-thio-3-succinimidyl-N-methylcyclohexyl-4-trans-carboxylic acid (9) and (S*)-Maytansin-3-N-methyl-L-alanine-propanamidyl-3-thio-3-succinimidyl-N-methylcyclohexyl-4-trans-carboxylic acid (10) (S* and R* Represent a Single Stereoisomer of Unknown Chirality)

The diastereomeric mixture of compounds 8 (20 mg) was dissolved in 0.5 ml of acetonitrile and separated using semi-prep Chiral column (Chirlacel OJ, Solvent system, 6:1:1 Hexanes:IPA:Ethanol) to afford 3.5 mg of 10 as the faster-running compound, MS m/z: 977.2 [MH+], 957.2 [M−18], 999.2 [M+Na]; Purity: >95% (by LC/MS), RT=32 min and 4.6 mg of 9 as the slower-running compound, MS m/z: 977.2 [MH+], 957.2 [M−18], 999.2 [M+Na]; Purity: >95% (by LC/MS), Rf=48 min.

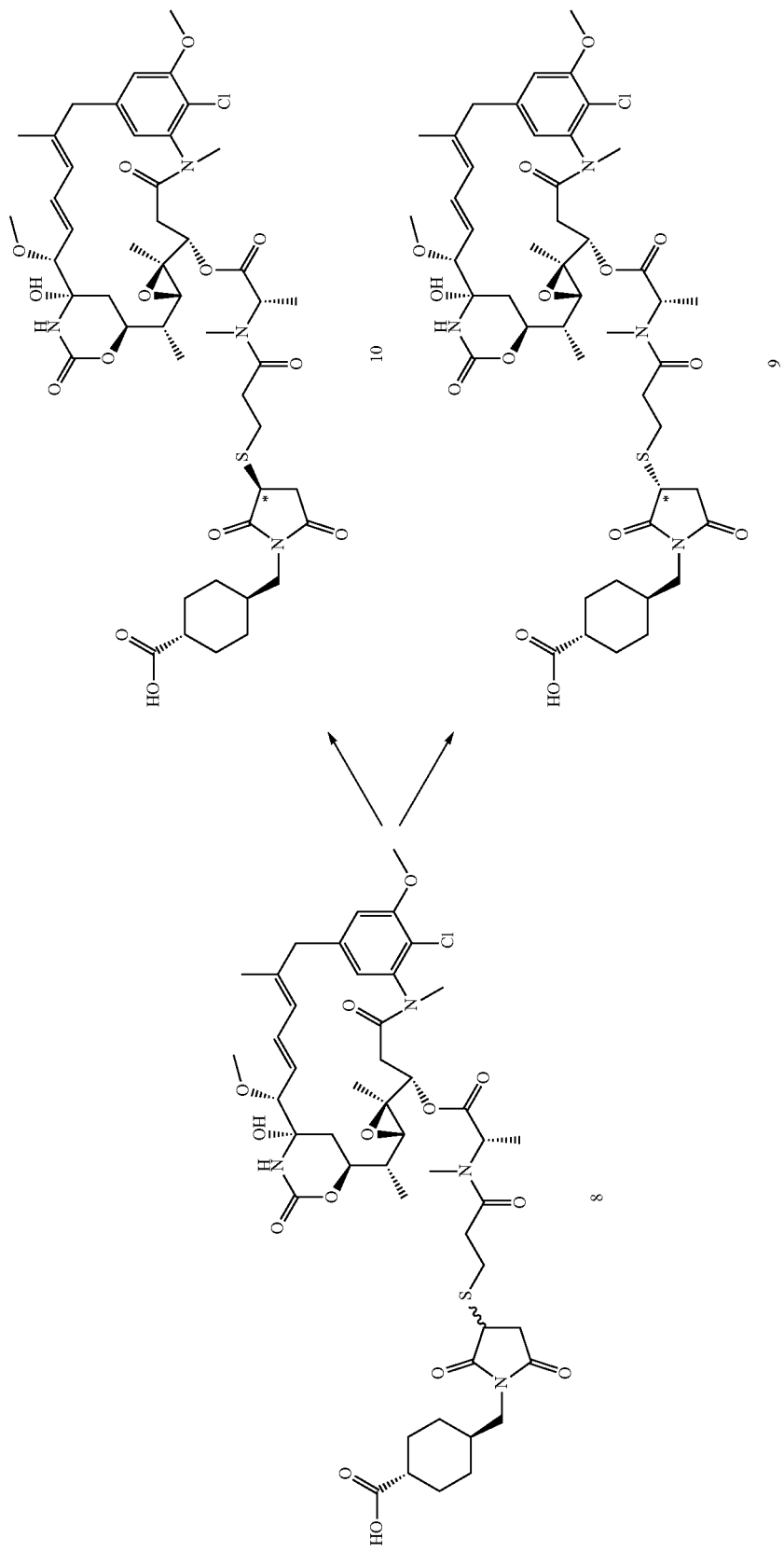

Example 6

Synthesis of (S*)-Maytansin-3-N-methyl-L-alanine-propanamidyl-3-thio-3-succinimidyl-N-methylcyclohexyl-4-trans-carboxylic acid (11)

A solution of 10 (2.5 mg, 0.0026 mmol) was dissolved in dichloromethane (1 mL), then treated with N-hydroxysuccinimide (NHS, 6.0 mg, 0.052 mmol) and 1-[3-(dimethylamino) propyl]-3-ethylcarbodiimide hydrochloride (EDCI, 13 mg, 0.065 mmol). The reaction mixture was stirred overnight at room temperature under argon, washed with water followed by brine, dried over anhydrous sodium sulfate, and filtered. The solvent was evaporated under reduced pressure to give the crude residue, which was purified by reverse phase chromatography using a C18, 20-40 micron column (30 g), eluting with a gradient (10-95% over 18 min) of acetonitrile (0.1% AcOH) in water (0.1% AcOH), and lyophilized to afford 11. MS m/z: 1073.2 [MH+], 1054.4[M−18]; Purity: 95% (by LC/MS).

Example 7

(R*)-Maytansin-3-N-methyl-L-alanine-propanamidyl-3-thio-3-succinimidyl-N-methylcyclohexyl-4-trans-carboxylicacid (12)

A solution of 9 (3, mg, 0.003 mmol) was dissolved in dichloromethane (1 mL), then treated with N-hydroxysuccinimide (NHS, 3.0 mg, 0.026 mmol) and 1-[3-(dimethylamino) propyl]-3-ethylcarbodiimide hydrochloride (EDCI, 7 mg, 0.036 mmol). The reaction mixture was stirred overnight at room temperature under argon, washed with water followed by brine, dried over anhydrous sodium sulfate, and filtered. The solvent was evaporated under reduced pressure to give the crude residue, which was purified by reverse phase chromatography using C18 column, 20-40 micron (15 g), eluting with a gradient (10-95% over 18 min) of acetonitrile (0.1% AcOH) in water (0.1% AcOH), lyophilized to afford 12. MS m/z: 1073.2 [MH+], 1054.4[M−18]; Purity: 95% (by LC/MS).

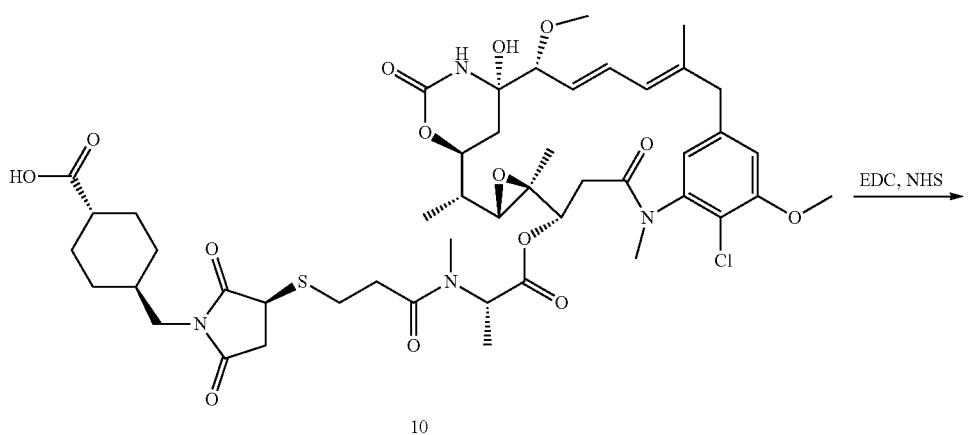

10

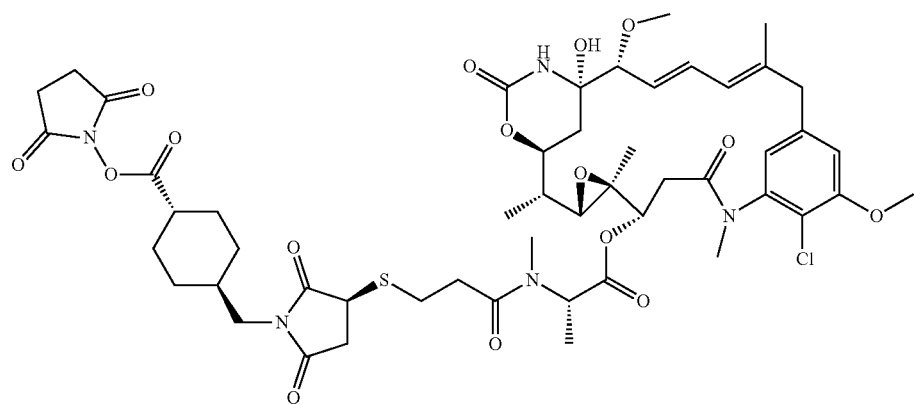

11

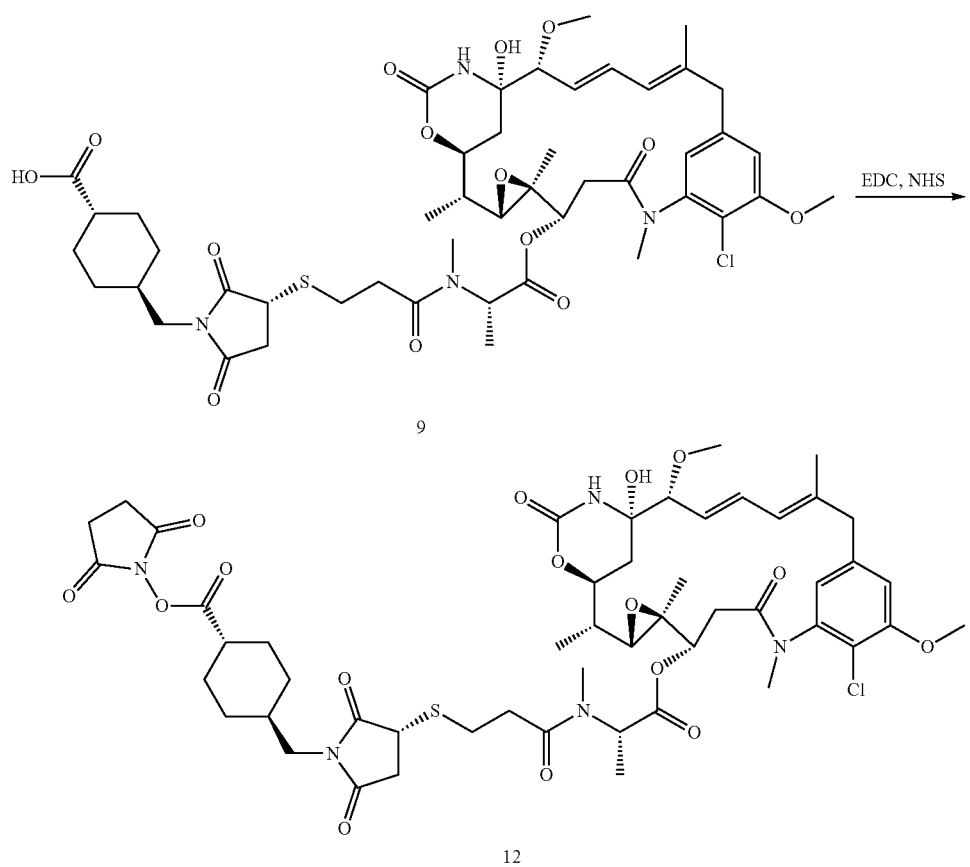

Example 8

Conjugate Preparation and Characterization.

Two different maytansine-linker compositions prepared according to the previous Examples (Compound 5 and Compound 6) were conjugated to various anti-tumor antigen monoclonal antibodies. Compound 5 comprises predominantly a single diastereomer of the linker-DM1 cytotoxic compound, whereas Compound 6 comprises a mixture of various linker-DM1 diastereomers. The antibodies used in this Example were an anti-HER2 antibody having variable regions derived from humAb4D5-8 from Carter et al, PNAS 1992 89 4285, an anti-EGFRvIII antibody having variable regions derived from clone 131 from WO2013075048 A1, and an anti-MUC16 antibody having variable regions derived from clone 3A5 from WO2007001851.

The antibodies were expressed in CHO cells and purified by Protein A. A non-binding isotype control antibody derived from an infectious disease antigen having no relation to oncology was also used in this Example.

The antibodies (10 mg/ml) in 50 mM HEPES, 150 mM NaCl, pH 8.0, and 10% (v/v) DMA were conjugated with a 6 fold excess of compound 5 or 6 for 1 hour at ambient temperature. The conjugates were purified by size exclusion chromatography and sterile filtered. Protein and linker payload concentrations were determined by UV spectral analysis and MALDI-TOF mass spectrometry. Size-exclusion HPLC established that all conjugates used were >95% monomeric, and RP-HPLC established that there was <0.5% unconjugated linker payload. Yields are reported in Table 1 based on protein. All conjugated antibodies were analyzed by UV for linker payload loading values according to Hamblett et al, Cancer Res 2004 10 7063 and by mass difference, native versus conjugated. The results are summarized in Table 1.

TABLE 1

| | $\epsilon252$ nm (cm$^{-1}$ M$^{-1}$) | $\epsilon280$ nm (cm$^{-1}$ M$^{-1}$) |
|---|---|---|
| Compound | | |
| 5 | 26790 | 5700 |
| 6* | 26790 | 5700 |
| Antibody | | |
| HER2 | 81847 | 215388 |
| EGFRvIII | 79579 | 209420 |
| MUC16 | 88671 | 248380 |
| Isotype Control | 81718 | 233480 |

| Antibody Conjugate | Payload:Antibody (UV) | Payload:Antibody (MS) | Yield % |
|---|---|---|---|
| HER2-5 (in vivo) | 2.7 | 2.7 | 66 |
| HER2-5 (in vitro) | 3.1 | 2.4 | 75 |
| HER2-6 (in vitro) | 2.9 | 2.4 | 70 |
| EGFRvIII-5 | 2.8 | 2.3 | 56 |
| EGFRvIII-6 | 2.9 | 2.2 | 56 |
| MUC16-5 | 2.4 | 2.0 | 76 |
| MUC16-6 | 2.3 | 2.1 | 96 |
| Isotype Control-5 | 3.3 | 3.3 | 67 |

*Extinction coefficients were used from compound 5

Example 9

In Vitro Cytotoxicity Assays.

Cells were seeded in PDL-coated 96 well plates at 10,000 (SK-BR-3 and NCI-$N_{87}$), 15,000 (BT-474), 3000 (Ovcar-3 and PC3/Muc16), 2000 (HEK293/hEGFRvIII), 1500 (U251/hEGFRvIII), or 400 (MMT/hEGFRvIII) cells per well in complete growth media and grown overnight. For cell viability curves, serially diluted antibody-drug conjugates or free payload were added to the cells at final concentrations ranging from 1 µM to 1 pM and incubated for 3 days. Each concentration was run in duplicate and reported with the respective standard deviation. Cells were incubated with CCK8 (Dojindo) for the final 1-3 h and the absorbance at 450 nm ($OD_{450}$) was determined on a Flexstation3 (Molecular Devices). Background $OD_{450}$ levels from digitonin (40 nM) treated cells were subtracted from all wells and viability is expressed as a percentage of the untreated controls. $IC_{50}$ values were determined from a four-parameter logistic equation over a 10-point response curve (GraphPad Prism). All curves and $IC_{50}$ values are corrected for payload equivalents based on the loading from the MALDI-TOF experiment.

Figure 3:
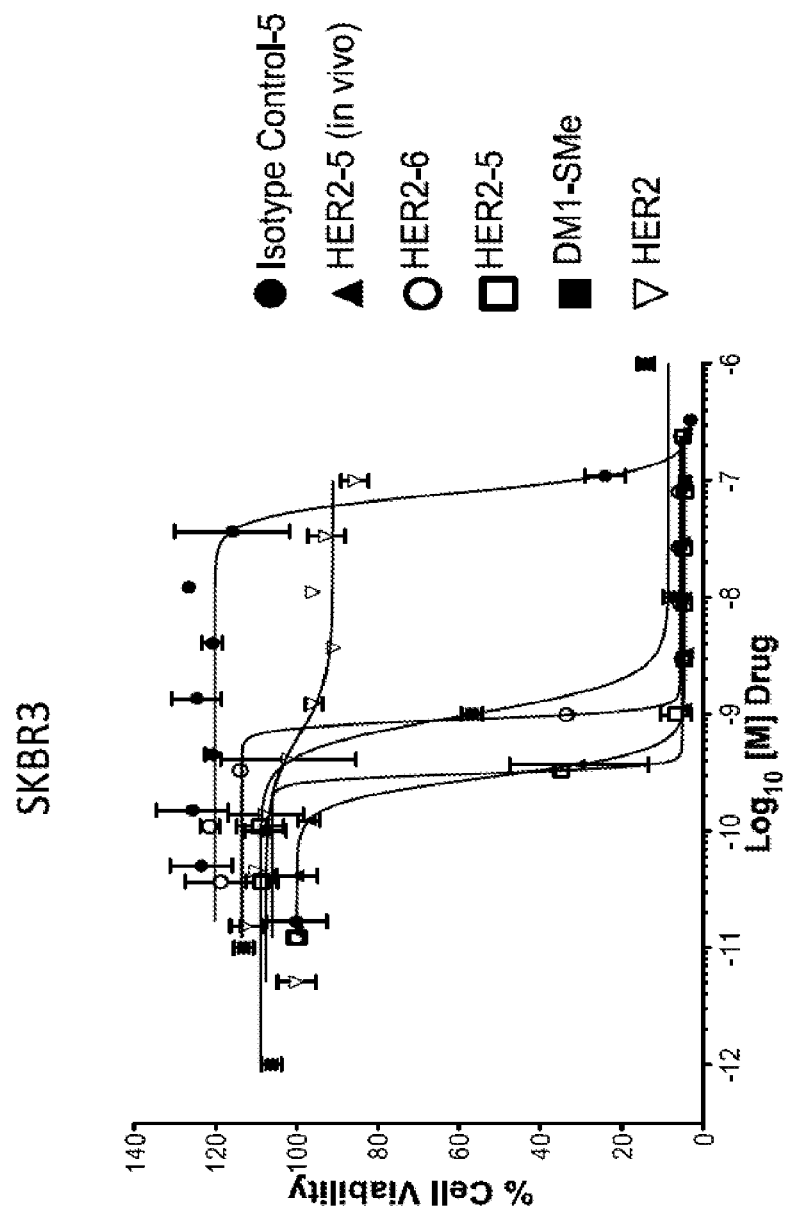
FIG. 3 illustrates that in SKBR3 cells the single diastereomer compound conjugate HER2-5 (in vitro and in vivo lots) possessed an IC50 value of 0.3 nM versus 0.9 nM for the mixture of diastereomer conjugate HER2-6.

In SKBR3 cells (breast cancer line), natively expressing HER2 at 607 fold above isotype control binding, the single diastereomer compound conjugate HER2-5 (in vitro and in vivo lots) possessed an $IC_{50}$ value of 0.3 nM versus 0.9 nM for the mixture of diastereomer compound conjugate HER2-6 (Table 2, FIG. 3). A small in vitro lot was conjugated first and only used for cell proliferation assays, while a larger in vivo lot was then conjugated and used for both in vitro and in vivo experiments. The naked HER2 antibody had little anti-proliferation activity.

Figure 4:
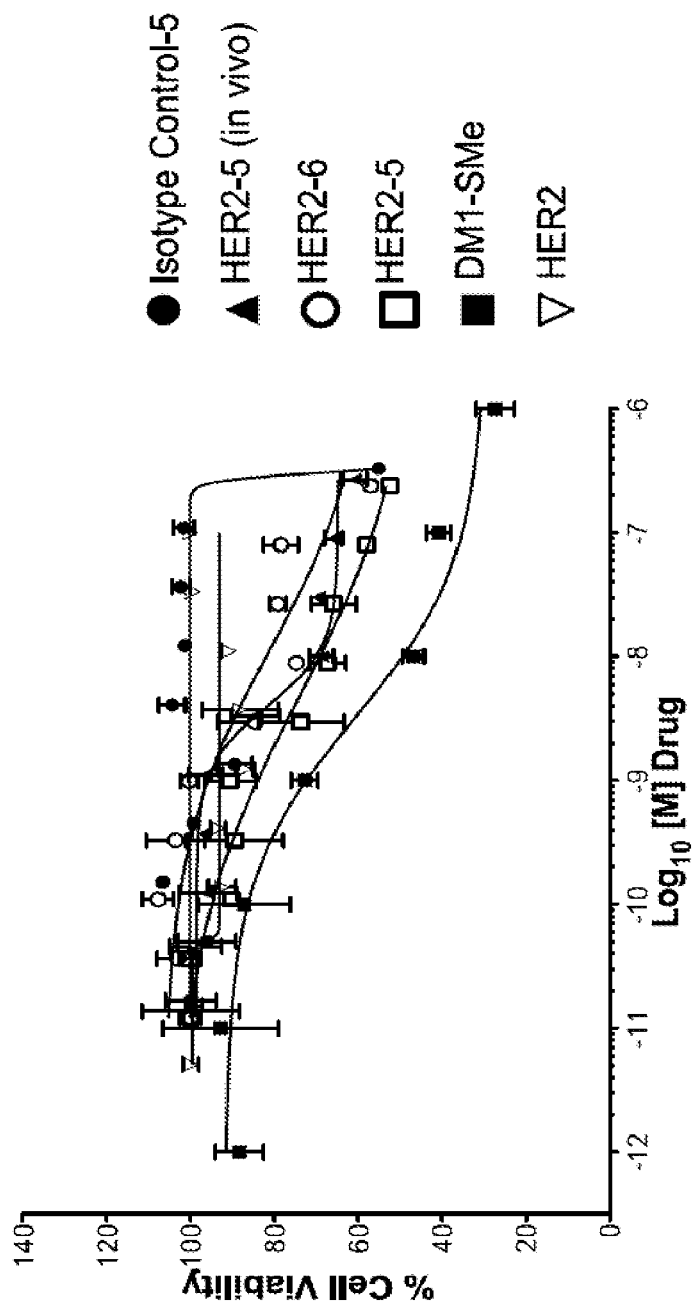
FIG. 4 illustrates that in BT474 cells the single diastereomer compound conjugate HER2-5 (in vitro) in possessed an $IC_{50}$ value of 4.6 nM while the HER2-5 (in vivo) lot had an $IC_{50}$ value of 4.0 nM versus 11.6 nM for the mixture of diastereomer conjugate HER2-6.

In BT474 cells (breast cancer line), natively expressing HER2 at 426 fold above isotype control binding, the single diastereomer compound conjugate HER2-5 (in vitro) possessed an $IC_{50}$ value of 4.6 nM while the HER2-5 (in vivo) lot had an $IC_{50}$ value of 4.0 nM versus 11.6 nM for the mixture of diastereomer compound conjugate HER2-6 (Table 2, FIG. 4). The naked HER2 antibody had little anti-proliferation activity.

Figure 5:
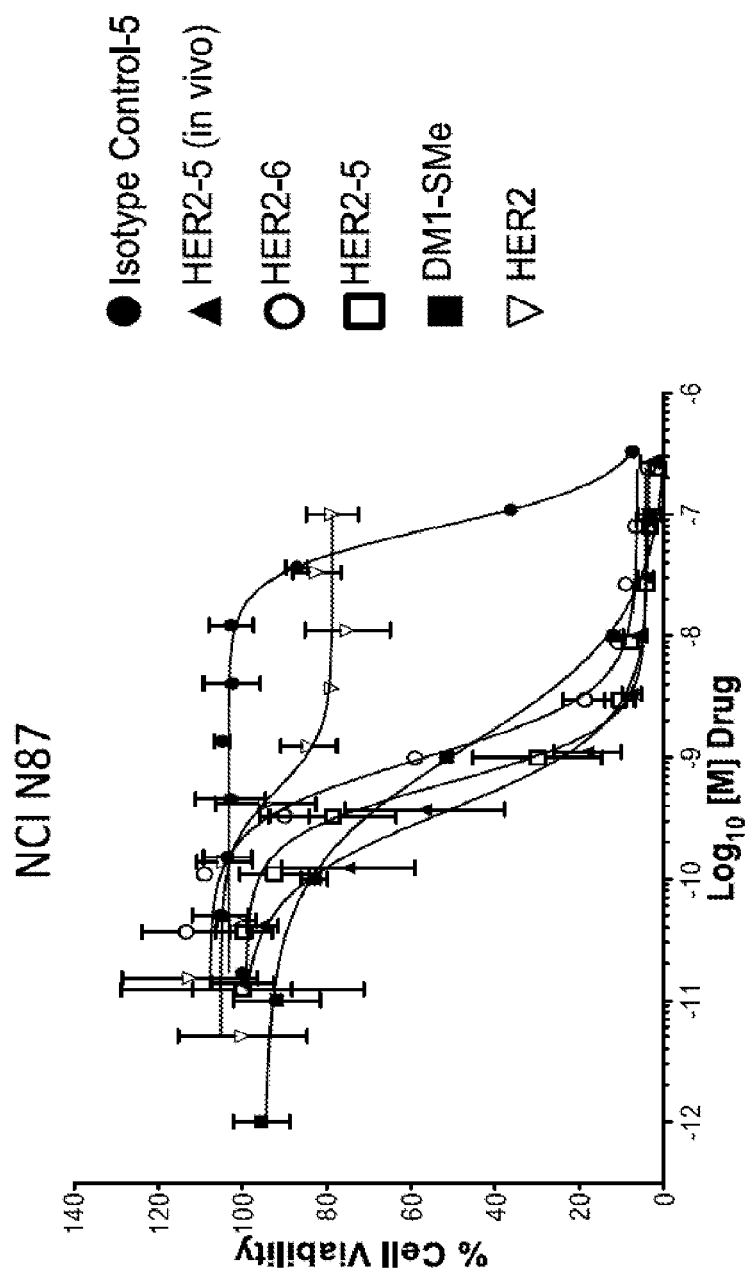
FIG. 5 illustrates that in NCI-N87 cells the single diastereomer compound conjugate HER2-5 (in vitro) possessed an $IC_{50}$ value of 0.6 nM while the HER2-5 (in vivo) lot had an $IC_{50}$ value of 0.4 nM versus 1.0 nM for the mixture of diastereomer conjugate HER2-6.

In NCI-N87 cells (breast cancer line), natively expressing HER2 at 869 fold above isotype control binding, the single diastereomer compound conjugate HER2-5 (in vitro) possessed an $IC_{50}$ value of 0.6 nM while the HER2-5 (in vivo) lot had an $IC_{50}$ value of 0.4 nM versus 1.0 nM for the mixture of diasteromer compound conjugate HER2-6 (Table 2, FIG. 5). The naked HER2 antibody had little anti-proliferation activity.

Figure 6:
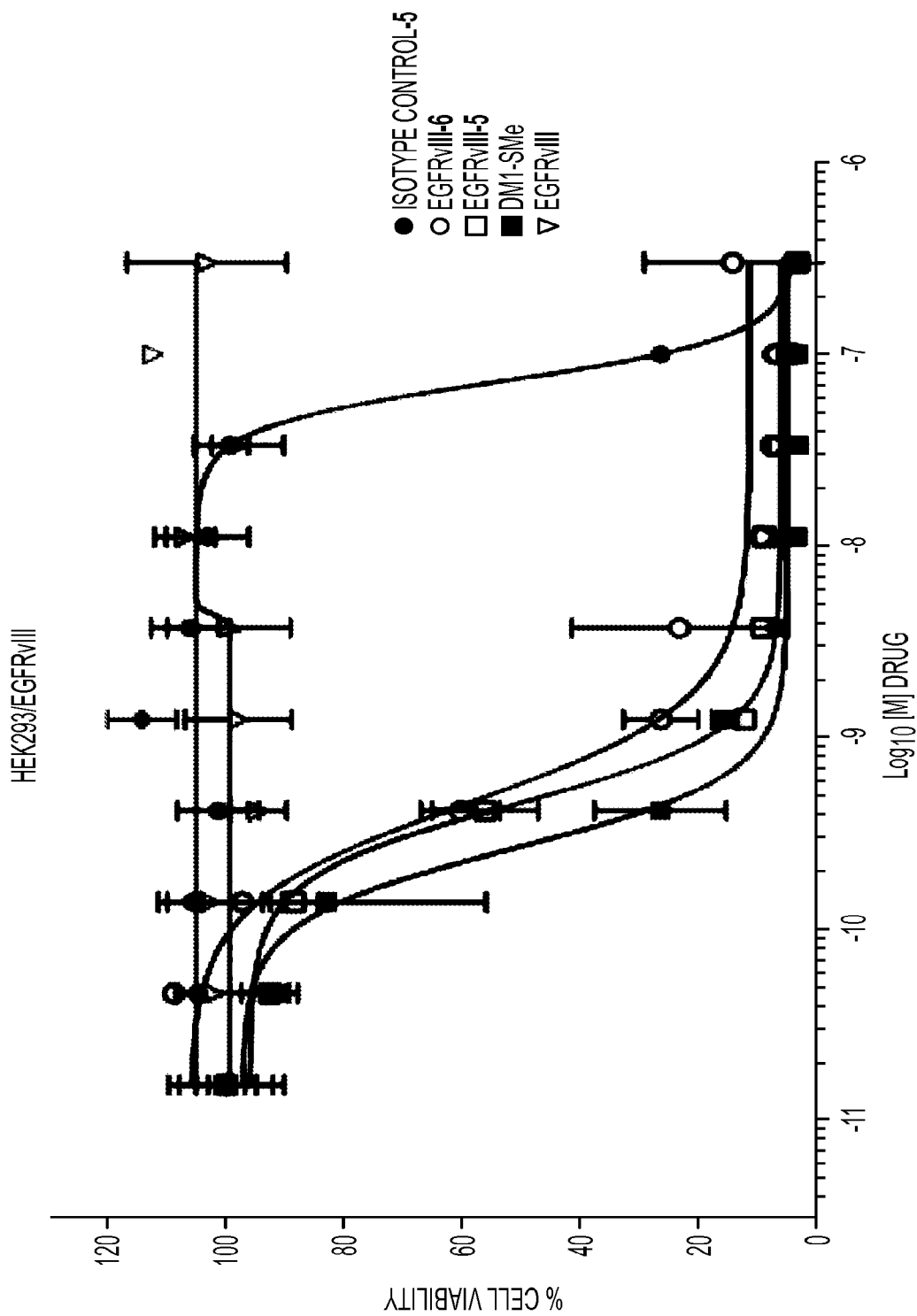
FIG. 6 illustrates that in HEK293/hEGFRvIII cells the single diastereomer compound conjugate EGFRvIII-5 possessed an $IC_{50}$ value of 0.4 nM while the mixture of diastereomer conjugate EGFRvIII-6 had an $IC_{50}$ value of 0.5 nM.

In HEK293/hEGFRvIII cells, expressing hEGFRvIII at 360 fold above isotype control binding, both conjugates (single and mixture of diastereomer) exhibited $IC_{50}$ values of 0.4 nM (Table 3, FIG. 6). The naked EGFRvIII antibody had little anti-proliferation activity.

Figure 7:
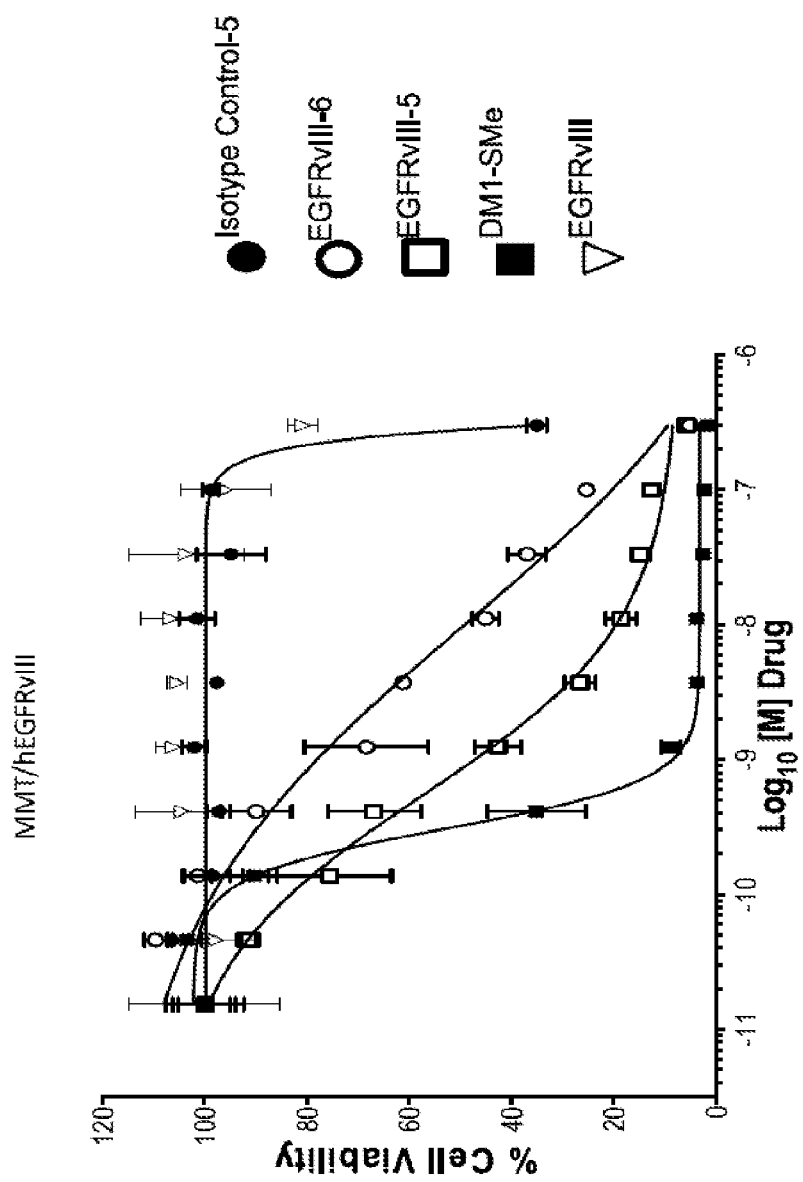
FIG. 7 illustrates that in MMT/hEGFRvIII cells the single diastereomer compound conjugate EGFRvIII-5 possessed an $IC_{50}$ value of 0.5 nM while the mixture of diastereomer conjugate EGFRvIII-6 had an $IC_{50}$ value almost 20 fold higher at 9.8 nM.

In MMT/hEGFRvIII cells, expressing hEGFRvIII at 280 fold above isotype control binding, the single diastereomer compound conjugate EGFRvIII-5 possessed an $IC_{50}$ value of 0.5 nM while the mixture of diastereomer compound conjugate EGFRvIII-6 had an $IC_{50}$ value of 9.8 nM (Table 2, FIG. 7). The naked EGFRvIII antibody had little anti-proliferation activity.

In U251/hEGFRvIII cells, expressing hEGFRvIII at 165 fold above isotype control binding, the single diasteromer compound conjugate EGFRvIII-5 possessed an $IC_{50}$ value of 2.4 nM while the mixture of diastereomer compound conjugate EGFRvIII-6 had an $IC_{50}$ value of 3.3 nM (Table 3, FIG. 7). The naked EGFRvIII antibody had little anti-proliferation activity.

Figure 8:
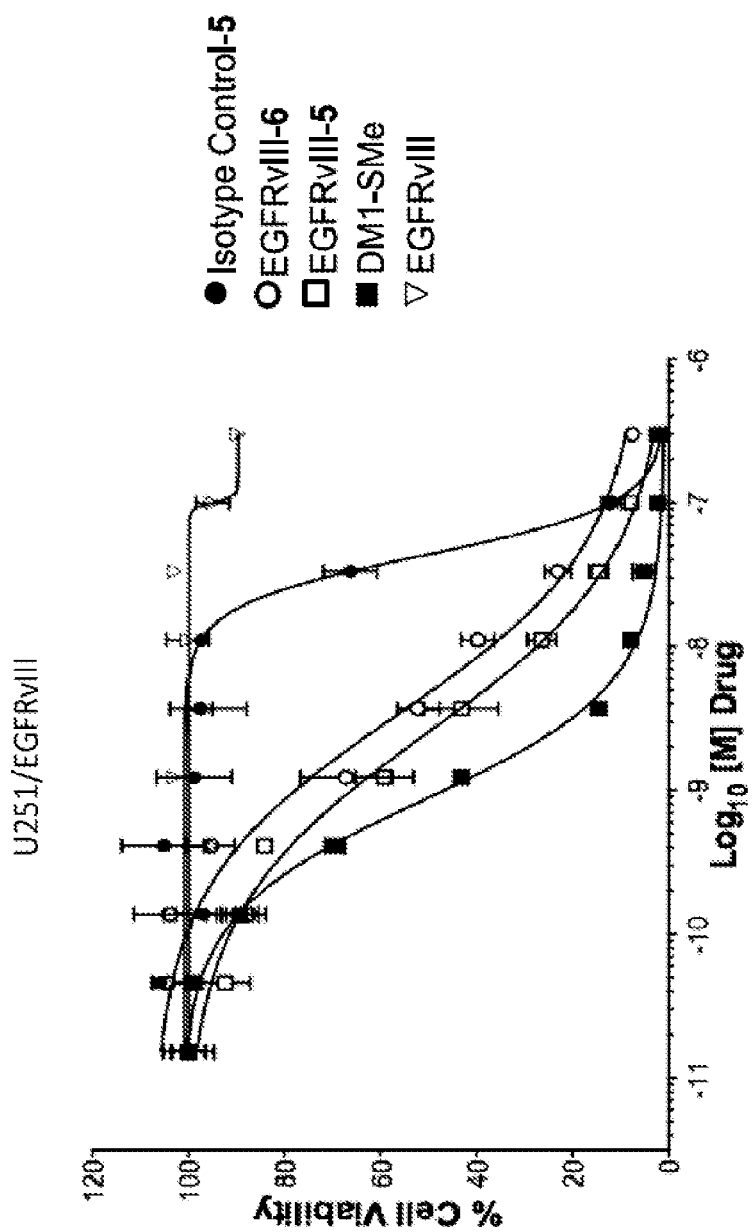
FIG. 8 illustrates that in U251/hEGFRvIII cells the single diastereomer compound conjugate EGFRvIII-5 possessed an $IC_{50}$ value of 2.4 nM while the mixture of diastereomer conjugate EGFRvIII-6 had an $IC_{50}$ value of 3.3 nM.

In Ovcar-3 cells (ovarian cancer line), natively expressing MUC16 at 373 fold above isotype control binding, the single diastereomer compound conjugate MUC16-5 possessed an $IC_{50}$ value of 6.3 nM while the mixture of diasteromer compound conjugate MUC16-6 had an $IC_{50}$ value of 16.0 nM (Table 4, FIG. 8). The naked Muc16 antibody had little anti-proliferation activity.

Figure 9:
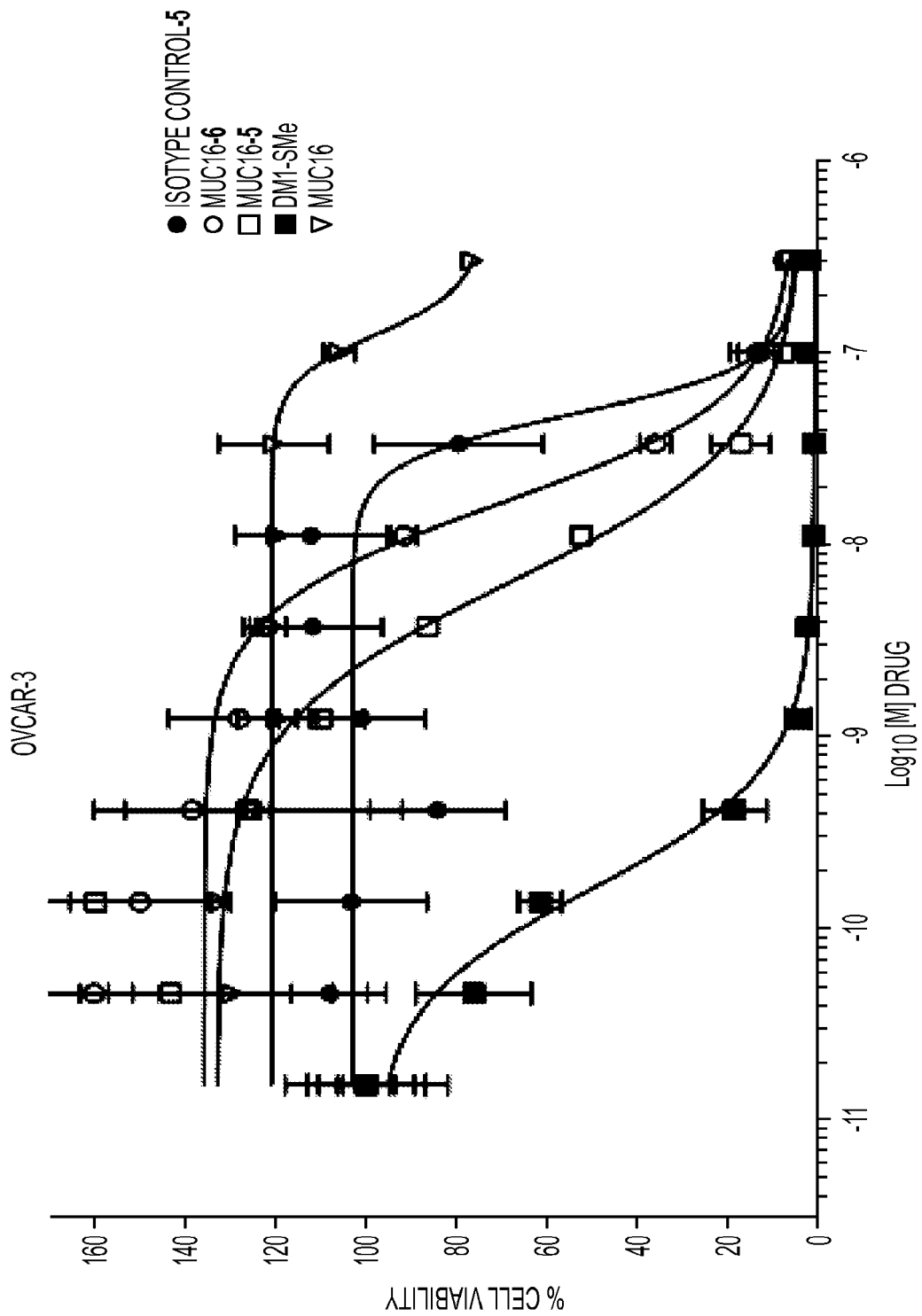
FIG. 9 illustrates that in Ovcar-3 cells the single diastereomer compound conjugate MUC16-5 possessed an $IC_{50}$ value of 6.3 nM while the mixture of diastereomer conjugate MUC16-6 had an $IC_{50}$ value of 16.0 nM.
Figure 10:
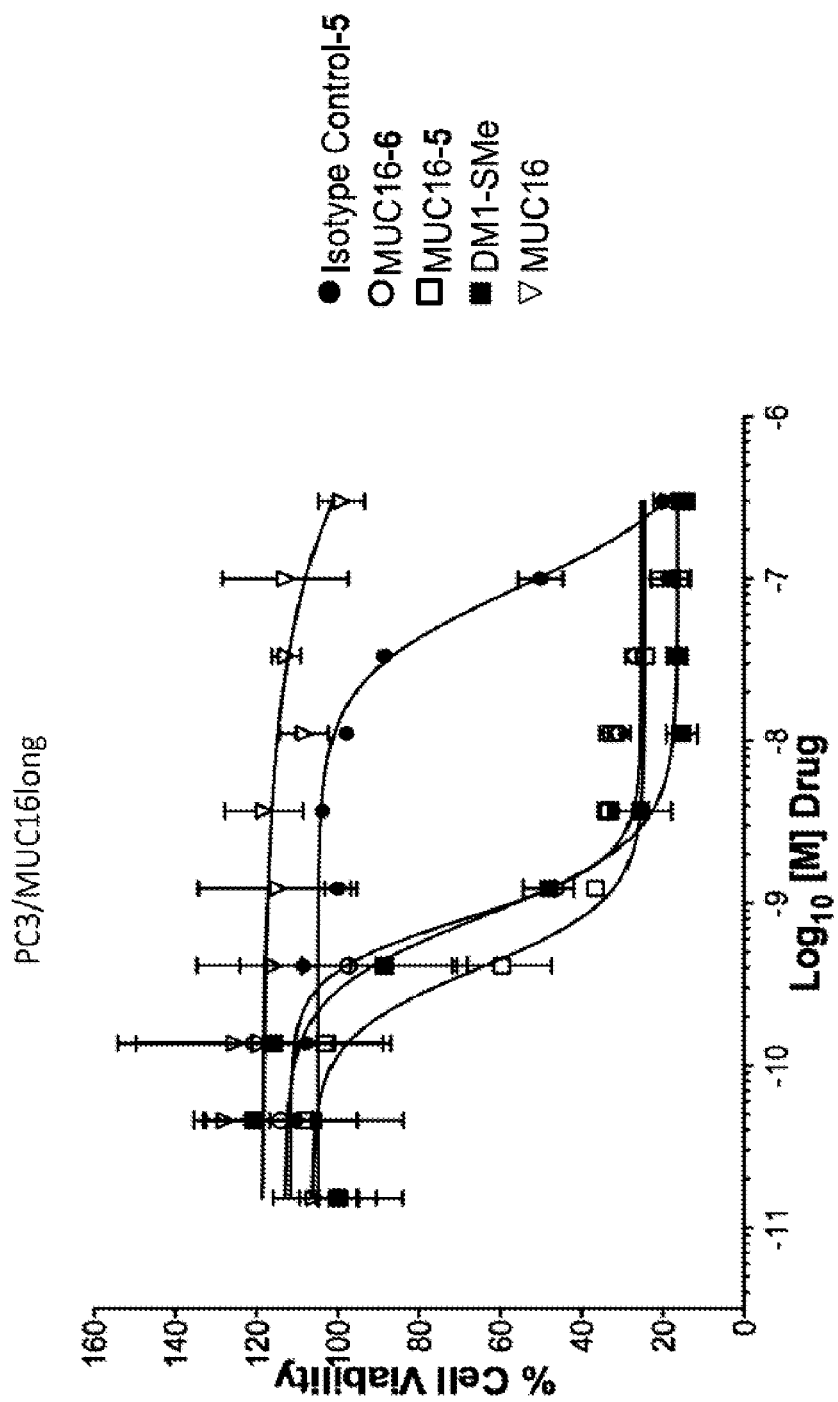
FIG. 10 illustrates that in PC3/MUC16 long cells the single diastereomer compound conjugate MUC16-5 in possessed an $IC_{50}$ value of 0.34 nM while the mixture of diastereomer conjugate MUC16-6 had an $IC_{50}$ value at 0.80 nM.

In PC3/MUC16 cells, expressing MUC16 at 105 fold above isotype control binding, the single diastereomer compound conjugate MUC16-5 possessed an $IC_{50}$ value of 0.34 nM while the mixture of diastereomer compound conjugate MUC16-6 had an $IC_{50}$ value of 0.8 nM (Table 4, FIG. 9). The naked Muc16 antibody had little anti-proliferation activity.

In FIGS. 3, 4, and 5 maytansin-3-N-methyl-L-Ala-(3-methyldisulfanyl) propanamide (DM1-SMe, prepared according to Ho and Carrozzella, U.S. Pat. Appl. 2007/0037972 A1) was chosen to represent the payload in these assays. Compound 4 would be too reactive to use in vitro or in vivo, thereby giving unreliable results.

The in vitro results are summarized in Tables 2-4 on a target basis below. This Example demonstrates that anti-tumor antibody-drug conjugates comprising the single diastereomer drug of the present invention, in most cases, exhibited greater in vitro killing potency than the corresponding antibody-drug conjugates comprising mixture of diastereomers. For the targets analyzed, the single diastereomer antibody-drug conjugates were typically on the order of 2- to 3-fold more potent than the corresponding mixture conjugates, depending on the particular cell lines tested.

TABLE 2

| Antibody Conjugate | SKBR3 IC50 (nM) | BT474 IC50 (nM) | N87 IC50 (nM) |
| --- | --- | --- | --- |
| HER2-5 (in vivo) | 0.3 | 4.0 | 0.4 |
| HER2-5 (in vitro) | 0.3 | 4.6 | 0.6 |
| HER2-6 (in vitro) | 0.9 | 11.6 | 1.0 |

TABLE 3

| Antibody Conjugate | HEK293/hEGFRvIII IC50 (nM) | MMT/hEGFRvIII IC50 (nM) | U251/hEGFRvIII IC50 (nM) |
| --- | --- | --- | --- |
| EGFRvIII-5 | 0.4 | 0.5 | 2.4 |
| EGFRvIII-6 | 0.5 | 9.8 | 3.3 |

TABLE 4

| Antibody Conjugate | Ovcar-3 IC50 (nM) | PC3/MUC16 IC50 (nM) |
| --- | --- | --- |
| MUC16-5 | 6.3 | 0.34 |
| MUC16-6 | 16.0 | 0.80 |

Example 10

In Vivo Studies.

To determine the in vivo efficacy of the anti-HER2 single-diastereomer conjugate ("HER2-5"), studies were performed in mice bearing HER2+ gastric cancer xenografts, as efficacy had been previously reported in this model by Barok et al (Barok M et al, Can Letters 2011). Specifically, $5 \times 10^6$ NCI-N87 cells (ATCC CRL-5822) were implanted subcutaneously into the lower right flank of CB-17 SCID mice (Taconic). Once tumors had reached an average volume of 150 mm$^3$, mice were randomized in to groups of eight and dosed with HER2-5 or control reagents. Control reagents included PBS vehicle, free DM1-SMe, isotype control, isotype control-5, or HER2. Mice received once weekly doses for three weeks and tumor volumes and body weights were monitored twice weekly throughout the study. Conjugates were dosed at 1, 5 and 15 mg/kg, as these doses had been shown to be effective in previous in vivo studies by Lewis-Phillips et al (Lewis-Phillips G et al., Can Res 2008).

Figure 11:
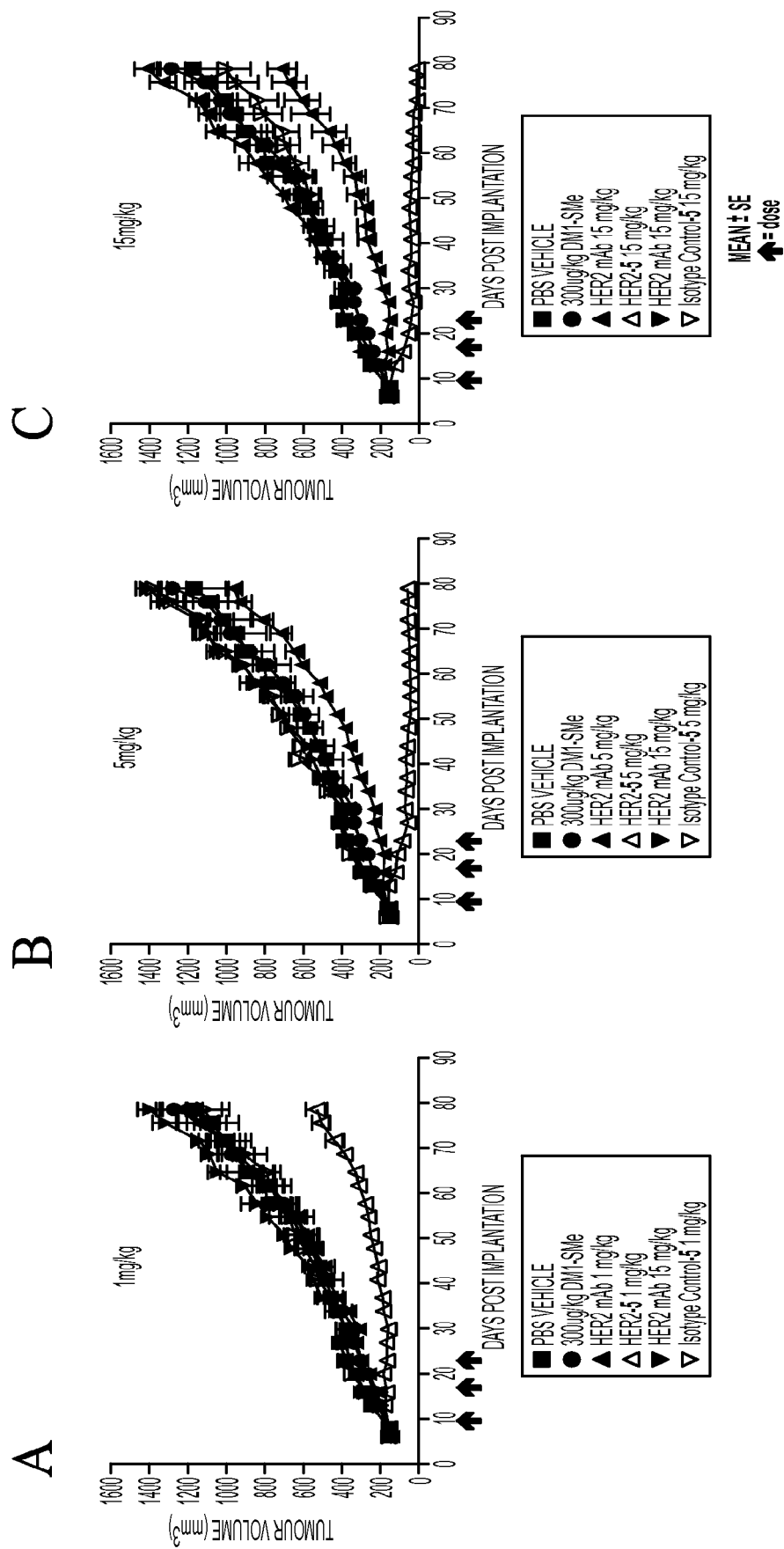
FIG. 11 illustrates tumor growth curves in mice following dosing with HER2-5 and control reagents. Mice received PBS vehicle (■), 300 ug/kg DM1-SMe (●) and Isotype Control mAb at 15 mg/kg (▼). Mice also received HER2 mAb (▲), HER2-5 (Δ) and Isotype Control-5 (∇) at doses of 1 mg/kg (A), 5 mg/kg (B) and 15 mg/kg (C). Mice received 3 once weekly doses of conjugates and control agents as indicated by the black arrows (↑. Groups are N=8, Mean±SE.).
Figure 12:
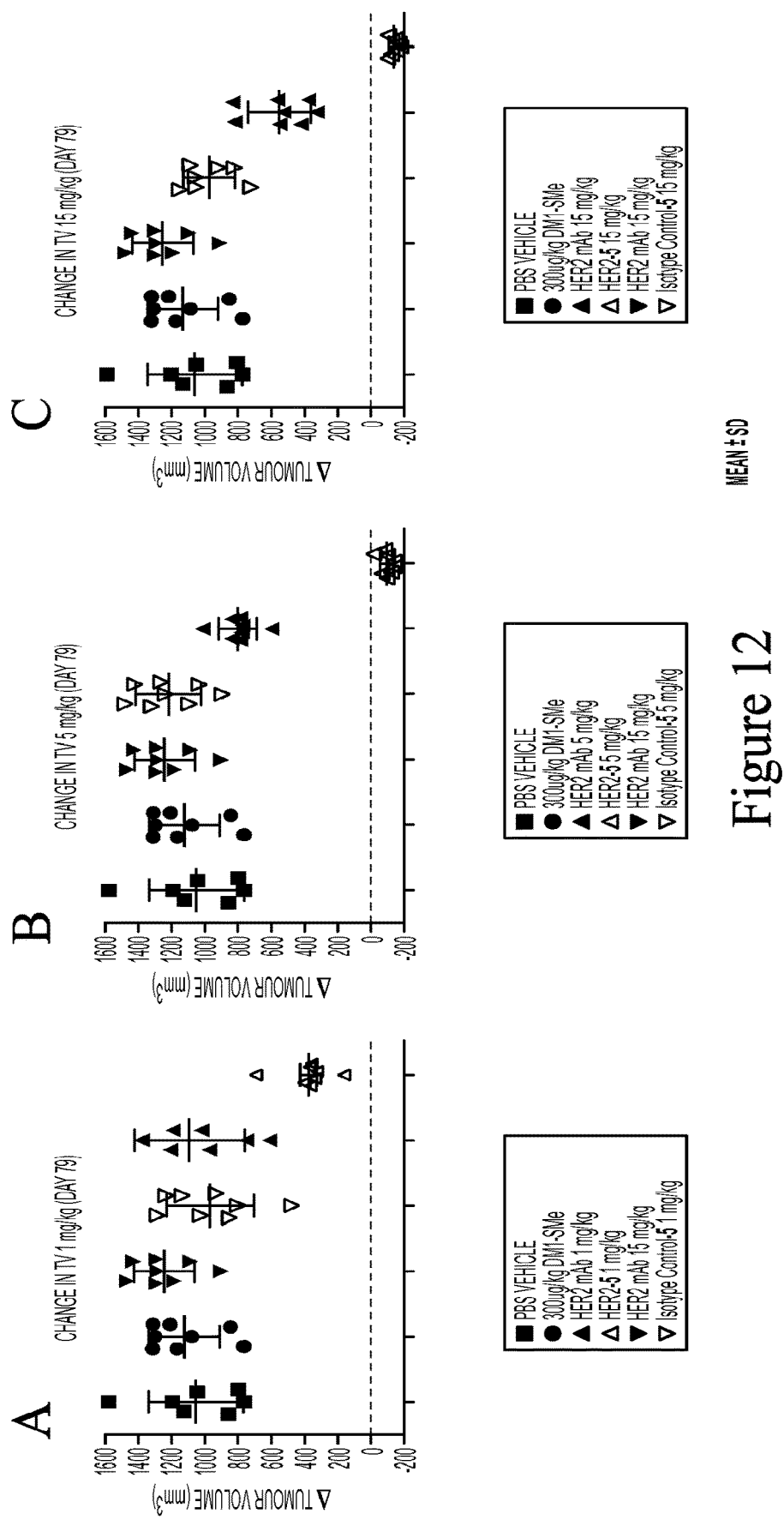
FIG. 12 illustrates change in tumor volume following dosing with HER2-5 and control reagents at termination of the PBS vehicle control group on Day 79 post tumor implantation. Individual tumor sizes are shown for each dosing group. Mice received PBS vehicle (■), 300 ug/kg DM1-SMe (●) and Isotype Control mAb at 15 mg/kg (▼). Mice also received HER2 mAb (▲), HER2-5 (Δ) and Isotype Control-5 (∇) at doses of 1 mg/kg (A), 5 mg/kg (B) and 15 mg/kg (C). Groups are N=8, Mean±SD.
Figure 13:
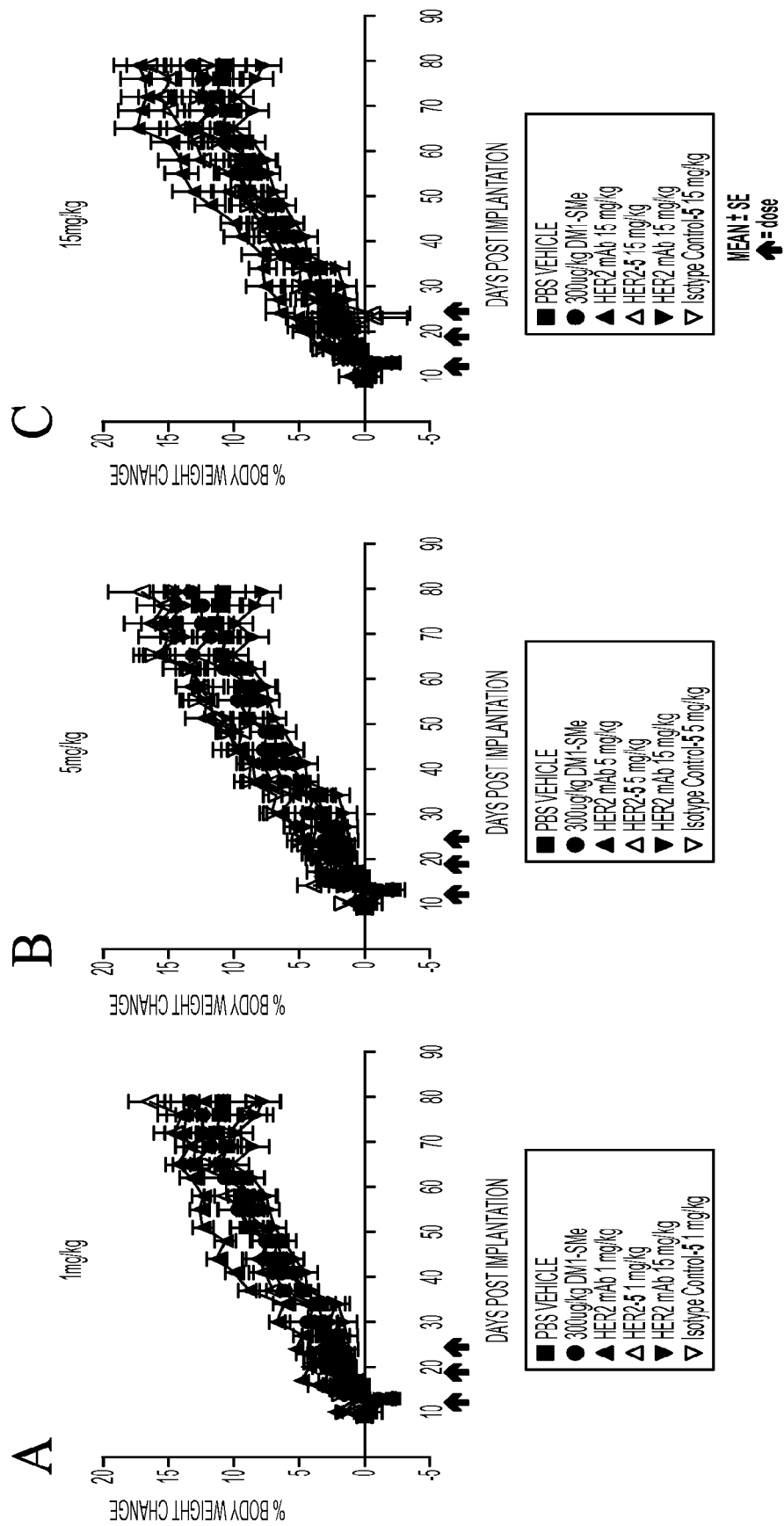
FIG. 13 illustrates percentage change in animal weights following dosing with HER2-5 and control reagents. Mice received PBS vehicle (■), 300 ug/kg DM1-SMe (●) and Isotype Control mAb at 15 mg/kg (▼). Mice also received HER2 mAb (▲), HER2-5 (Δ) and Isotype Control-5 (∇) at doses of 1 mg/kg (∇), 5 mg/kg (B) and 15 mg/kg (C). Mice received 3 once weekly doses of conjugates and control agents as indicated by the black arrows (T. Groups are N=8, Mean±SE.).

In the current N87 tumor model, HER2-5 demonstrated clear anti-tumor efficacy, with doses of 5 and 15 mg/kg leading to significant decreases in initial tumor volume and eradication of some tumors at the higher dose (FIGS. 11 and 12). A significant delay in tumor growth relative to control agents was also observed in the 1 mg/kg dose level. No adverse events were observed following dosing, with mice receiving HER2-5 demonstrating robust weight gain throughout the study (FIG. 13).

What is claimed is:

1. A diastereomer of Formula I

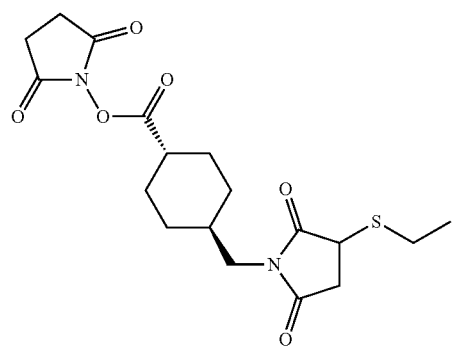

(I)

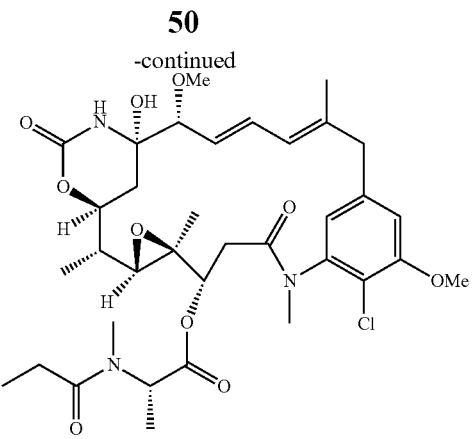

wherein the diastereomer is characterized by a $^1$H NMR characterized by delta shifts of (300 MHz, CDCl$_3$) δ 6.85 (d, 1H, J=4 Hz), 6.72 (m, 1H), 6.65 (d, 1H, J=4 Hz), 6.44 (dd, 1H, J=15 Hz, 11 Hz), 6.25 (s, 1H), 5.67 (dd, 1H, J=16 Hz, 9 Hz), 5.41 (m, 1H), 4.79 (d, 1H, J=11 Hz), 4.30 (t, 1H, J=11 Hz), 3.72 (m, 2H), 3.51 (d, 1H, J=9 Hz), 3.37 (m, 4H), 3.27 (m, 1H), 3.23 (s, 3H), 3.16-2.99 (m, 4H), 2.85 (m, 7H), 2.62 (m, 3H), 2.39 (ddd, 1H, J=19 Hz, 12 Hz, 4 Hz), 2.18 (br m, 2H), 1.77 (br m, 3H), 1.66 (s, 3H), 1.60-1.47 (m, 4H), 1.31 (m, 6H), 1.05 (m, 2H), and 0.82 (s, 3H); and wherein the diastereomer characterized by the delta shifts is present in a diastereomeric excess of more than 90%, and wherein the diastereomeric excess is based on a composition comprising a mixture of at least two diastereomers having different stereochemical configurations at the chiral carbon that is bound to the sulfur atom of Formula I.

2. A compound of Formula I

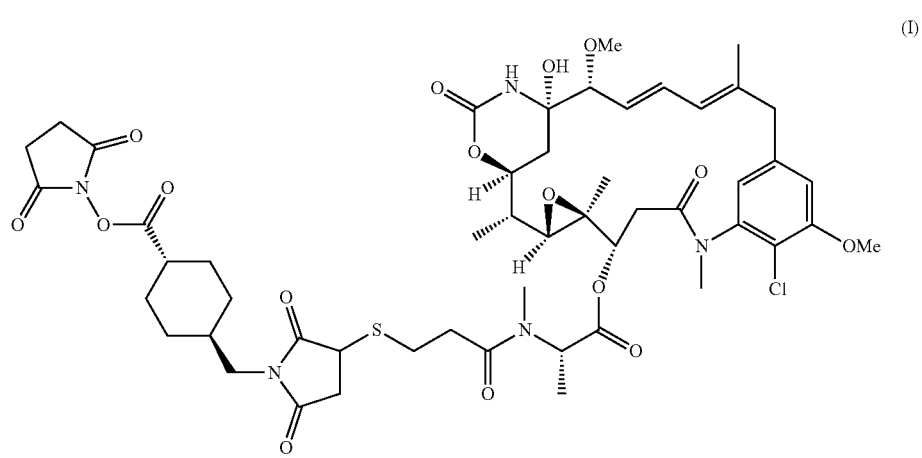 [SMILES: COc1cc2cc(c1Cl)N(C)C(=O)C[C@H](OC(=O)[C@H](C)N(C)C(=O)CCSC1CC(=O)N(C[C@H]3CC[C@H](C(=O)ON4C(=O)CCC4=O)CC3)C1=O)[C@]1(C)O[C@H]1[C@H](C)[C@@H]1C[C@@](O)(NC(=O)O1)[C@H](OC)/C=C/C=C(\C)C2]

(I)

wherein the compound is characterized by a ¹H NMR characterized by delta shifts of (300 MHz, CDCl₃) δ 6.85 (d, 1H, J=4 Hz), 6.72 (m, 1H), 6.65 (d, 1H, J=4 Hz), 6.44 (dd, 1H, J=15 Hz, 11 Hz), 6.25 (s, 1H), 5.67 (dd, 1H, J=16 Hz, 9 Hz), 5.41 (m, 1H), 4.79 (d, 1H, J=11 Hz), 4.30 (t, 1H, J=11 Hz), 3.72 (m, 2H), 3.51 (d, 1H, J=9 Hz), 3.37 (m, 4H), 3.27 (m, 1H), 3.23 (s, 3H), 3.16-2.99 (m, 4H), 2.85 (m, 7H), 2.62 (m, 3H), 2.39 (ddd, 1H, J=19 Hz, 12 Hz, 4 Hz), 2.18 (br m, 2H), 1.77 (br m, 3H), 1.66 (s, 3H), 1.60-1.47 (m, 4H), 1.31 (m, 6H), 1.05 (m, 2H), and 0.82 (s, 3H); and wherein the compound characterized by the delta shifts is present in a diastereomeric excess of more than 90%, and wherein the diastereomeric excess is based on a composition comprising a mixture of at least two diastereomers having different stereochemical configurations at the chiral carbon that is bound to the sulfur atom of Formula I;

prepared by a process comprising the steps of
  (a) contacting
    (i) a compound of Formula III

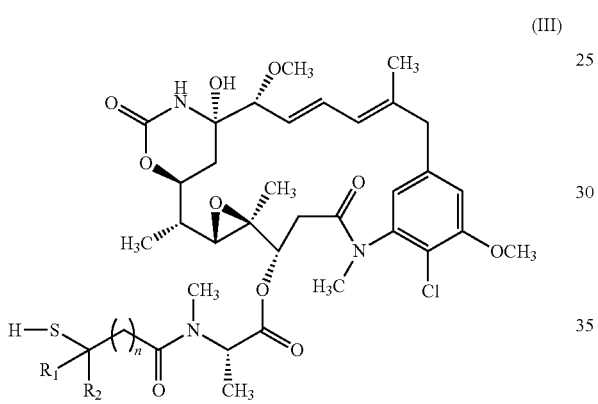

(III)

wherein R₁ and R₂ are hydrogen; and
n is one;

(ii) a compound of Formula IV

(IV)

wherein Y¹ is

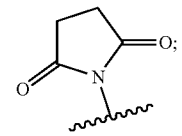 [SMILES: *N1C(=O)CCC1=O]

(iii) silica gel;
(iv) a diluent comprising an organic solvent and water; and
(b) isolating the compound of Formula I.

3. An antibody-drug conjugate prepared by contacting a compound of Formula I

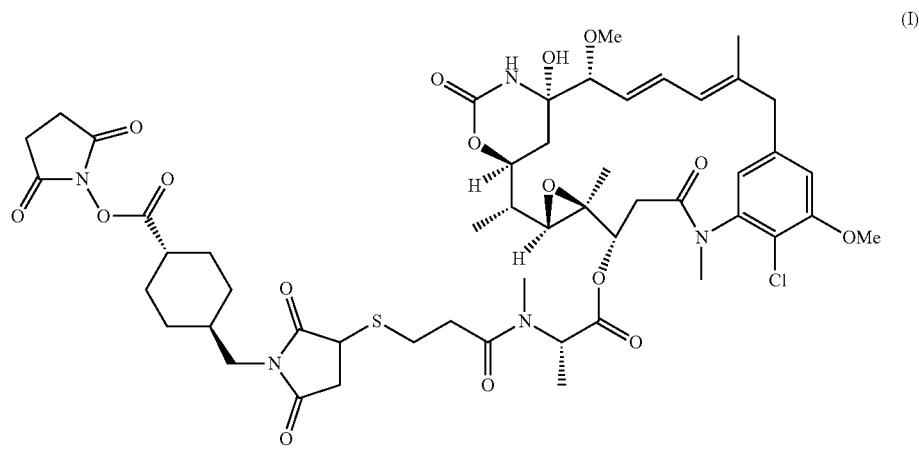 [SMILES: COc1cc2cc(c1Cl)N(C)C(=O)C[C@H](OC(=O)[C@H](C)N(C)C(=O)CCSC1CC(=O)N(C[C@H]3CC[C@H](C(=O)ON4C(=O)CCC4=O)CC3)C1=O)[C@]1(C)O[C@H]1[C@H](C)[C@@H]1C[C@@](O)(NC(=O)O1)[C@H](OC)/C=C/C=C(\C)C2]

(I)

wherein the compound is characterized by a $^1$H NMR characterized by delta shifts of (300 MHz, CDCl$_3$) δ 6.85 (d, 1H, J=4 Hz), 6.72 (m, 1H), 6.65 (d, 1H, J=4 Hz), 6.44 (dd, 1H, J=15 Hz, 11 Hz), 6.25 (s, 1H), 5.67 (dd, 1H, J=16 Hz, 9 Hz), 5.41 (m, 1H), 4.79 (d, 1H, J=11 Hz), 4.30 (t, 1H, J=11 Hz), 3.72 (m, 2H), 3.51 (d, 1H, J=9 Hz), 3.37 (m, 4H), 3.27 (m, 1H), 3.23 (s, 3H), 3.16-2.99 (m, 4H), 2.85 (m, 7H), 2.62 (m, 3H), 2.39 (ddd, 1H, J=19 Hz, 12 Hz, 4 Hz), 2.18 (br m, 2H), 1.77 (br m, 3H), 1.66 (s, 3H), 1.60-1.47 (m, 4H), 1.31 (m, 6H), 1.05 (m, 2H), and 0.82 (s, 3H); and wherein the compound characterized by the delta shifts is present in a diastereomeric excess of more than 90%, and wherein the diastereomeric excess is based on a composition comprising a mixture of at least two diastereomers having different stereochemical configurations at the chiral carbon that is bound to the sulfur atom of Formula I;

with an antibody or antigen-binding fragment thereof, wherein the compound of Formula I is prepared by a process comprising the steps of (a) contacting (i) a compound of Formula III

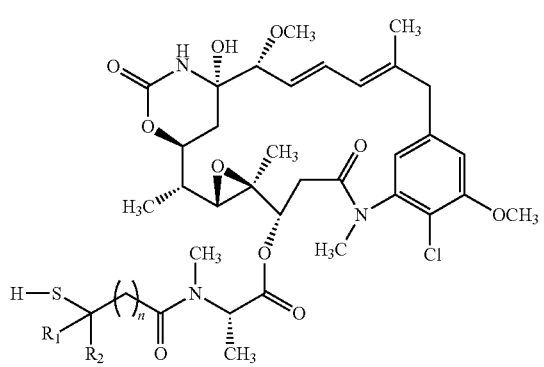

wherein R$_1$ and R$_2$ are hydrogen; and n is one;

(ii) a compound of Formula IV

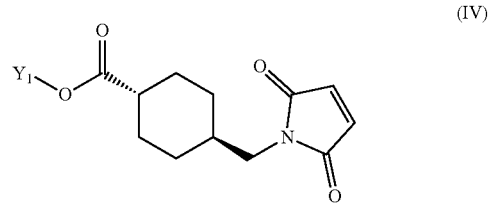

(IV)

wherein Y$^1$ is

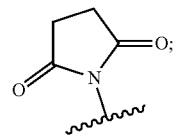

(iii) silica gel;

(iv) a diluent comprising an organic solvent and water; and (b) isolating the antibody-drug conjugate of Formula I.

4. The antibody-drug conjugate of claim 3, wherein the antibody or antigen-binding fragment thereof specifically binds a tumor-associated antigen and further wherein the tumor-associated antigen is selected from the group consisting of AFP, ALK, BAGE proteins, β-catenin, brc-abl, BRCA1, BORIS, CA9, carbonic anhydrase IX, caspase-8, CD20, CD40, CDK4, CEA, CLEC12A, cMET, CTLA4, cyclin-B1, CYP1B1, EGFR, EGFRvIII, ErbB2/Her2, ErbB3, ErbB4, ETV6-AML, EphA2, Fra-1, FOLR1, GAGE proteins, GD2, GD3, GloboH, glypican-3, GM3, gp100, Her2, HLA/B-raf, HLA/k-ras, HLA/MAGE-A3, hTERT, IGF1R, LGR5, LMP2, MAGE proteins (e.g., MAGE-1, -2, -3, -4, -6, and -12), MART-1, mesothelin, ML-IAP, Muc1, Muc16 or CA-125, MUM1, NA17, NY-BR1, NY-BR62, NY-BR85, NY-ESO1, OX40, p15, p53, PAP, PAX3, PAX5, PCTA-1, PDGFR-α, PDGFR-β, PDGF-A, PDGF-B, PDGF-C, PDGF-D, PLAC1, PRLR, PRAME, PSMA, FOLH1, RAGE proteins, Ras, RGS5, Rho, SART-1, SART-3, Steap-1, Steap-2, survivin, TAG-72, TGF-β, TMPRSS2, Tn, TNFRSF17, TRP-1, TRP-2, tyrosinase, and uroplakin-3.

5. A process for preparing a compound of Formula I

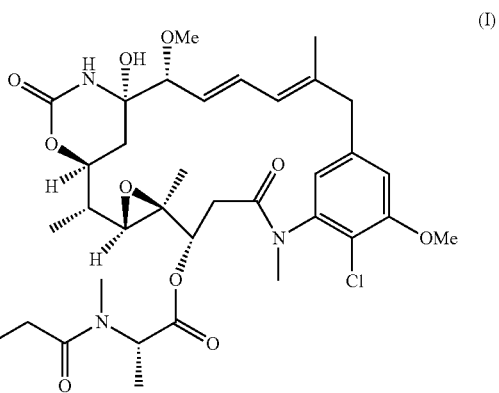

(I)

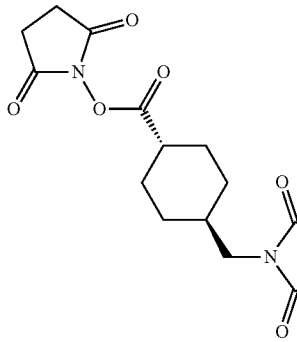

wherein the compound of Formula I is characterized by a ¹H NMR characterized by delta shifts of (300 MHz, CDCl₃) δ 6.85 (d, 1H, J=4 Hz), 6.72 (m, 1H), 6.65 (d, 1H, J=4 Hz), 6.44 (dd, 1H, J=15 Hz, 11 Hz), 6.25 (s, 1H), 5.67 (dd, 1H, J=16 Hz, 9 Hz), 5.41 (m, 1H), 4.79 (d, 1H, J=11 Hz), 4.30 (t, 1H, J=11 Hz), 3.72 (m, 2H), 3.51 (d, 1H, J=9 Hz), 3.37 (m, 4H), 3.27 (m, 1H), 3.23 (s, 3H), 3.16-2.99 (m, 4H), 2.85 (m, 7H), 2.62 (m, 3H), 2.39 (ddd, 1H, J=19 Hz, 12 Hz, 4 Hz), 2.18 (br m, 2H), 1.77 (br m, 3H), 1.66 (s, 3H), 1.60-1.47 (m, 4H), 1.31 (m, 6H), 1.05 (m, 2H), and 0.82 (s, 3H); and wherein the compound characterized by the delta shifts is present in a diastereomeric excess of more than 90%, and wherein the diastereomeric excess is based on a composition comprising a mixture of at least two diastereomers having different stereochemical configurations at the chiral carbon that is bound to the sulfur atom of Formula I;

the process comprising the steps of
(a) contacting
a compound of Formula III

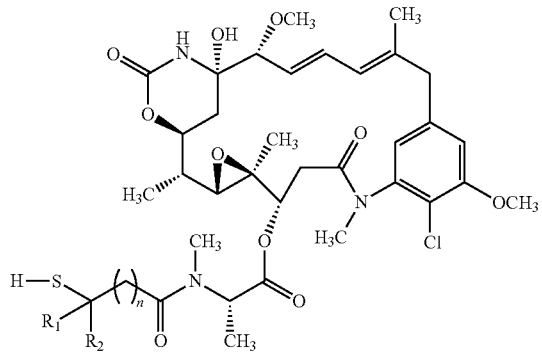

(III)

wherein R₁ and R₂ are hydrogen; and
n is one;
(ii) a compound of Formula IV

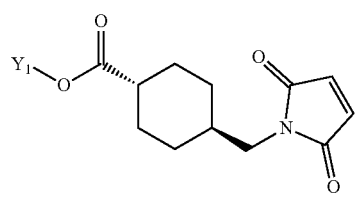

(IV)

wherein Y¹ is

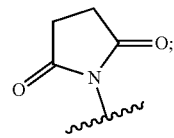 [SMILES: *N1C(=O)CCC1=O]

(iii) silica gel;
(iv) a diluent comprising an organic solvent and water; and
(b) isolating the compound of Formula (I).

6. The process of claim 5, wherein the organic solvent comprises a polar aprotic solvent.

7. The process of claim 6, wherein the polar aprotic solvent is acetonitrile.

8. The process of claim 5, wherein the molar ratio of the starting material having Formula III and the compound of Formula IV is from about 1:1 to about 1:3.

9. The process of claim 5, wherein the organic solvent and water are present in a ratio from about 1:1 to about 4:1, or from about 1:1 to about 10:1.

10. The process of claim 9, wherein the organic solvent is acetonitrile and the ratio of acetonitrile to water is about 4:1.

11. The process of claim 5, further comprising contacting the compound of Formula I of step (b) with an antibody or antigen-binding fragment thereof, to obtain an antibody-drug conjugate.

12. The antibody-drug conjugate of claim 11, wherein the antibody or antigen-binding fragment thereof specifically binds a tumor-associated antigen and further wherein the tumor-associated antigen is selected from the group consisting of AFP, ALK, BAGE proteins, β-catenin, brc-abl, BRCA1, BORIS, CA9, carbonic anhydrase IX, caspase-8, CD20, CD40, CDK4, CEA, CLEC12A, cMET, CTLA4, cyclin-B1, CYP1B1, EGFR, EGFRvIII, ErbB2/Her2, ErbB3, ErbB4, ETV6-AML, EphA2, Fra-1, FOLR1, GAGE proteins, GD2, GD3, GloboH, glypican-3, GM3, gp100, Her2, HLA/B-raf, HLA/k-ras, HLA/MAGE-A3, hTERT, IGF1R, LGR5, LMP2, MAGE proteins MAGE-1, MAGE-2, MAGE-3, MAGE-4, MAGE-6, MAGE-12, MART-1, mesothelin, ML-IAP, Muc1, Muc16 or CA-125, MUM1, NA17, NY-BR1, NY-BR62, NY-BR85, NY-ESO1, OX40, p15, p53, PAP, PAX3, PAX5, PCTA-1, PDGFR-α, PDGFR-β, PDGF-A, PDGF-B, PDGF-C, PDGF-D, PLAC1, PRLR, PRAME, PSMA, FOLH1, RAGE proteins, Ras, RGS5, Rho, SART-1, SART-3, Steap-1, Steap-2, survivin, TAG-72, TGF-β, TMPRSS2, Tn, TNFRSF17, TRP-1, TRP-2, tyrosinase, and uroplakin-3.

* * * * *